US012781214B2

(12) United States Patent
Parkinson et al.

(10) Patent No.: US 12,781,214 B2
(45) Date of Patent: Nov. 3, 2026

(54) BIOACTIVE PEPTIDE MOLECULES DISCOVERED BY A COMBINATION OF BIOINFORMATICS TECHNIQUE AND CHEMICAL SYNTHESIS

(71) Applicant: Purdue Research Foundation, West Lafayette, IN (US)

(72) Inventors: Elizabeth I. Parkinson, West Lafayette, IN (US); Matthew A. Hostetler, Huntington, WV (US)

(73) Assignee: Purdue Research Foundation, West Lafayette, IN (US)

( * ) Notice: Subject to any disclaimer, the term of this patent is extended or adjusted under 35 U.S.C. 154(b) by 436 days.

(21) Appl. No.: 18/525,840

(22) Filed: Nov. 30, 2023

(65) Prior Publication Data

US 2024/0101995 A1 Mar. 28, 2024

Related U.S. Application Data

(63) Continuation of application No. 17/679,249, filed on Feb. 24, 2022, now Pat. No. 11,879,142.

(60) Provisional application No. 63/156,393, filed on Mar. 4, 2021.

(51) Int. Cl.

| | |
|---|---|
| ***A61K 38/08*** | (2019.01) |
| ***C07K 7/64*** | (2006.01) |
| ***C12N 9/00*** | (2006.01) |
| ***C12P 21/02*** | (2006.01) |

(52) U.S. Cl.
CPC ................ *C12N 9/93* (2013.01); *A61K 38/08* (2013.01); *C07K 7/64* (2013.01); *C12P 21/02* (2013.01)

(58) Field of Classification Search
CPC .. C12N 9/93; A61K 38/08; C07K 7/64; C12P 21/02
See application file for complete search history.

(56) References Cited

U.S. PATENT DOCUMENTS 11,365,219 B2 * 6/2022 Heath ................ G01N 33/6842

FOREIGN PATENT DOCUMENTS

WO 20211042039 A1 3/2021
WO WO-2021042039 A1 * 3/2021 ............... C07K 7/64

OTHER PUBLICATIONS

Chu et al (Journal of American Chemical Society, 141(40): 15737-15741, 2019) (Year: 2019).*
Hostetler et al in "Synthetic natural product inspired cyclic peptides" (ACS Chemical Biology 2021, vol. 16 No. 11, pp. 2604-2611; published Oct. 26, 2021). (Year: 2021).*
Hostetler et al., Supporting Information, Synthetic Natural Product Inspired Cyclic Peptides, 2021, ACS Chemical Biology, 16: 2604-2611 (Year: 2021).*
Li, L. Accessing hidden microbial biosynthetic potential from underexplored sources for novel drug discovery, 2023, Biotechnology Advances, 66: 108716 (Year: 2023).*
Modi et al., Stapled Peptides as Direct Inhibitors of Nrf2-sMAF Transcription Factors, Journal of Medicinal Chemistry, 66: 6184-6192 (Year: 2023).*
Batista, J. M., and Nicu, V.P. Simplified and enhanced VCD analysis of cyclic peptides guided by artificial intelligence, 2023, Physical Chemistry Chemical Physics, 25: 22111-22116 (Year: 2023).*
Blin, K. et al., antiSMASH 5.0: updates to the secondary metabolite genome mining pipeline, Nucleic Acids Research, 47, pp. 81-87, 2019.
Chu, J. et al., Discovery of MRSA active antibiotics using primary sequence from the human microbiome, Nature Chemical Biology, 12, pp. 1004-1008, 2016.
Chu, J. et al., Bioactive Synthetic-Bioinformatic Natural Product Cyclic Peptides Inspired by Nonribosomal Peptide Synthetase Gene Clusters from the Human Microbiome, J. Am. Chem. Soc., 141, pp. 15737-15741, 2019.
Chu, J. et al., Synthetic-Bioinformatic Natural Product Antibiotics with Diverse Modes of Action, J. Am. Chem. Soc., 142, pp. 14158-14168, 2020.
Jad, Y. E. et al., Synthesis and Biological Evaluation of a Teixobactin Analogue, Org. Lett., 17, pp. 6182-6185, 2015.
Kuranaga, T. et al., Total Synthesis of the Nonribosomal Peptide Surugamide B and Identification of a New Offloading Cyclase Family, Angew. Chem. Int. Ed., 57, pp. 9447-9451, 2018.
Li, Y.-X. et al., Discovery of cationic nonribosomal peptides as Gram-negative antibiotics through global genome mining, Nature Communications, 9, pp. 1-9, 2018.
Newman, D. J. et al., Natural Products as Sources of New Drugs over the Nearly Four Decades from Jan. 1981 to Sep. 2019, J. Nat. Prod., 83, pp. 770-803, 2020.
Parmar, A. et al., Teixobactin analogues reveal enduracididine to be non-essential for highly potent antibacterial activity and lipid II binding, Chem. Sci., 8, pp. 8183-8192, 2017.
Pupin, M. et al., Norine: A powerful resource for novel nonribosomal peptide discovery, Synthetic and Systems Biotechnology, 1, pp. 89-94, 2016.
Qian, Z. et al., Enhancing the Cell Permeability and Metabolic Stability of Peptidyl Drugs by Reversible Bicyclization, Angew. Chem. Int. Ed., 56, pp. 1525-1529, 2017.

(Continued)

*Primary Examiner* — Catherine S Hibbert
(74) *Attorney, Agent, or Firm* — Purdue Research Foundation

(57) ABSTRACT

The present disclosure teaches a method of treating a patient in need of therapeutic intervention with bioactive cyclic peptide molecules which are useful as antimicrobials, anti-cancer agents, antiparasitic, immunosuppressants, and others.

1 Claim, 7 Drawing Sheets

(56) References Cited

OTHER PUBLICATIONS

Skinnider, M. A. et al., Genomes to natural products PRediction Informatics for Secondary Metabolomes (PRISM), Nucleic Acids Research, 43, pp. 9645-9662, 2015.
Skinnider, M. A. et al., Comprehensive prediction of secondary metabolite structure and biological activity from microbial genome sequences, Nature Communications, 11, pp. 1-9, 2020.
Mla-Farres, X. et al., Antimicrobials Inspired by Nonribosomal Peptide Synthetase Gene Clusters, J. Am. Chem. Soc., 139, pp. 1404-1407, 2017.
Zhou, Y. et al., Investigation of Penicillin Binding Protein (PBP)-like Peptide Cyclase and Hydrolase in Surugamide Non-ribosomal Peptide Biosynthesis, Cell Chemical Biology, 26, pp. 737-744, 2019.
Hostetler et al., Synthetic Natural Product Inspired Cyclic Peptides, 2021, ACS Chemical Biology, 16: 2604-2611 (Year: 2021).
Batista, J.M. et al., Simplified and enhanced VCD analysis of cyclic peptides guided by artificial intelligence, 2023, Physical Chemistry Chemical Physics, 25: 22111-22116 (Year: 2023).

* cited by examiner

FIG. 3

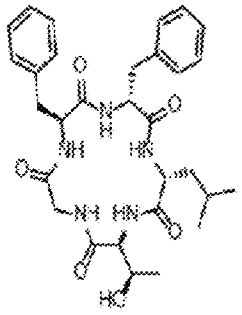

pNP-23
WP_125053638.1
*S. rimosus* subsp. *paromomycinus* ATCC 14827
Overall Yield: 42%

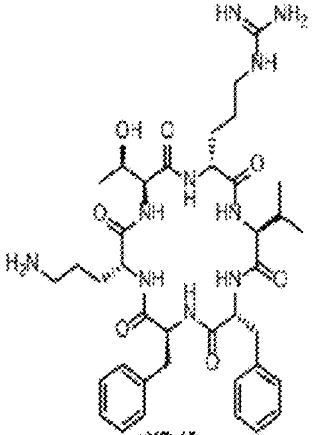

pNP-43
SDG84718.1
*Lentzea fradiae* CGMCC 4.3506
Overall Yield: 11%

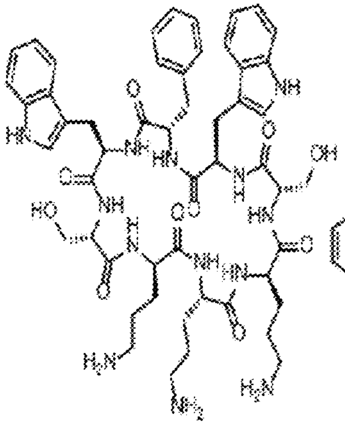

pNP-80
WP_043531424.1
*Actinoplanes utahensis* NRRL 12052
Overall Yield: 6%

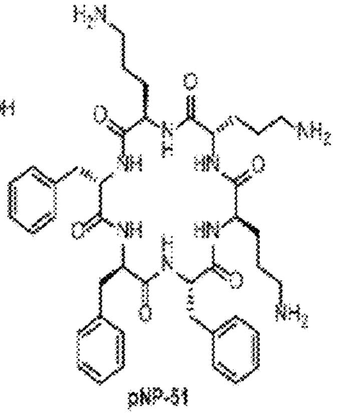

pNP-51
WP_056820610.1
*Allokutzneria* sp. NRRL B-24872
Overall Yield: 15%

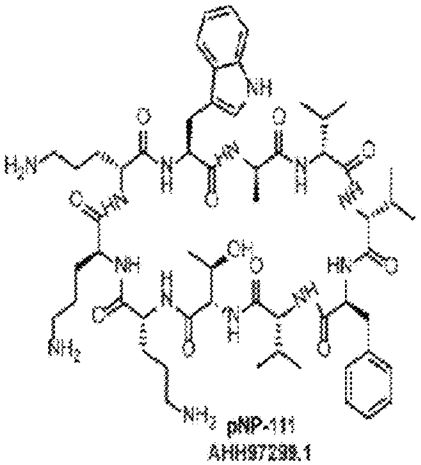

pNP-111
AHH97238.1
*Kutzneria albida* ATCC 25243
Overall Yield: 7%

| | *E. coli* | | *K. pneumoniae* | | *A. baumannii* | | *P. aeruginosa* | | Hemolysis | A549 toxicity |
|---|---|---|---|---|---|---|---|---|---|---|
| Compound | WT | R | WT | R | WT | R | WT | R | 53 µg/mL | 16 µg/mL |
| pNP-23 | 16 (28) | >32 (>57) | >32 (>57) | >32 (>57) | >32 (>57) | >32 (>57) | >32 (>57) | >32 (>57) | <10% | <50% death |
| pNP-43 | 32 (42) | 32 (42) | 32 (42) | >32 (>42) | 16 (21) | 32 (42) | >32 (>42) | >32 (>42) | <10% | <50% death |
| pNP-80 | 32 (31) | 32 (31) | 32 (31) | >32 (>31) | 16 (15) | 16-32 (15-31) | >32 (>31) | >32 (>31) | >10% | <50% death |
| pNP-51 | >32 (>41) | >32 (>41) | >32 (>41) | >32 (>41) | >32 (>41) | >32 (>41) | 32 (41) | 16 (20) | <10% | <50% death |
| pNP-111 | 32 (28) | 32 (28) | >32 (>28) | 32 (28) | >32 (>28) | 32 (28) | >32 (>28) | >32 (>28) | <10% | <50% death |
| Cipro | <0.1 (<1.4) | >32 (>87) | <0.1 (<1.4) | >32 (>87) | 1 (2.7) | >32 (>87) | 0.5-1.0 (1.4-2.7) | >32 | ND | ND |

Structure for SDG84710-1 BGC pNP-43

AA1
bulky
amino acid

AA2
aromatic
amino acid

AA3
aromatic
amino acid

AA6
positive
amino acid

AA4
positive
amino acid

AA5
flexible pNP-43d

BIOACTIVE PEPTIDE MOLECULES DISCOVERED BY A COMBINATION OF BIOINFORMATICS TECHNIQUE AND CHEMICAL SYNTHESIS

CROSS-REFERENCE TO RELATED APPLICATIONS

The present U.S. patent application is a continuation of U.S. patent application Ser. No. 17/679,249 filed Feb. 24, 2022, which relates to and claims the priority benefit of U.S. Provisional Patent Application Ser. No. 63/156,393, filed Mar. 4, 2021, the contents of which are hereby incorporated by reference in its entirety into this disclosure.

GOVERNMENT SUPPORT CLAUSE

This invention was made with government support under GM138002-01 awarded by the National Institutes of Health. The government has certain rights in the invention.

TECHNICAL FIELD

The present disclosure generally relates to bioactive peptide molecules discovered by a combination of bioinformatics technique and chemical synthesis.

BACKGROUND

This section introduces aspects that may help facilitate a better understanding of the disclosure. Accordingly, these statements are to be read in this light and are not to be understood as admissions about what is or is not prior art.

Natural products (NPs) have been a bountiful source of medicines including antimicrobials, anticancer agents, antiparasitics, immunosuppressants, as well as many others.[1] Historically, bacteria have been one of Nature's most prolific producers of biologically active NPs.[2] One important class of biologically active bacterial NPs are nonribosomal peptides (NRPs). These peptides are synthesized by modular enzyme complexes known as nonribosomal peptide synthetases (NRPS) and comprise a rich set of structurally diverse NPs, including many clinically used antibiotics such as daptomycin, bacitracin, polymyxin B, and colistin.[3] Cyclic peptides are an especially important class of NRPs, possessing many favorable pharmacological properties over their linear counterparts.[4-6] Their relatively large size and structural rigidity allow them to engage challenging targets, including protein-protein interactions.[4,7-9] Cyclic NRPs are also generally more cell permeable and resistant to proteases compared to linear peptides.[5,10,11] For these reasons, there is great interest in the discovery of additional cyclic NRPs as biological tools and drug leads.

BRIEF DESCRIPTION OF DRAWINGS

FIG. 2A) pNPs distribution with total number of cyclic peptides noted in light blue and the number of unique and novel cyclic peptides noted in dark blue. FIG. 2B) Tanimoto similarity data represented in tree form. Details of strains and molecules synthesized can be found in FIG. S2. FIG. 2C) Sequence Similarity Network for PBP-like cyclases. The size (number of amino acids) of the predicted cyclic peptide product is indicated by the color of the nodes. FIG. 2D) BiG-SCAPE network of PBP-like cyclase and NRPS containing BGCs. Each circle represents a family (closely related) of BGCs. Branches to other circles indicate clans (more distantly related BGCs). The size (number of amino acids) of the predicted cyclic peptide product is indicated by the color.

FIG. 3 shows the structures of pNPs that hit against Gram-negative bacteria. Gram-negative bacteria and a table describing their activities. The strains analyzed are described in the materials and methods section. Potencies of hits are given in μg/mL and in parentheses are the potency in μM. WT: wild type; R: antibiotic resistant; Cipro: ciprofloxacin; WT *E. coli*: ATCC 25922; R *E. coli*: ATCC BAA-2469; WT *K. pneumoniae*: ATCC 27736; R *K. pneumoniae*: ATCC BAA-21469; WT *A. baumannii*: ATCC 19606; R *A. baumannii*: KB349; WT *P. aeruginosa*: PAO1; R *P. aeruginosa*: PA1000. Hemolysis of human red blood cells and toxicity to the human cancer cell line A549 are also reported. ND=not determined.

FIG. 4A) NRPS BGC including the PBP-like cyclase SDG84710.1. FIG. 4B) NRPS modules and amino acid predictions by PRISM. AA # refer to the amino acid position of pNP-43.

FIG. 5A) Chemical structures of pNP-43d with basic residues indicated in red. FIG. 5B) Representative data from Sytox Green lysis assay with *A. baumannii* 19606. Error bars are standard deviation from 3 technical replicates. N=3.

DETAILED DESCRIPTION

Figure 1:
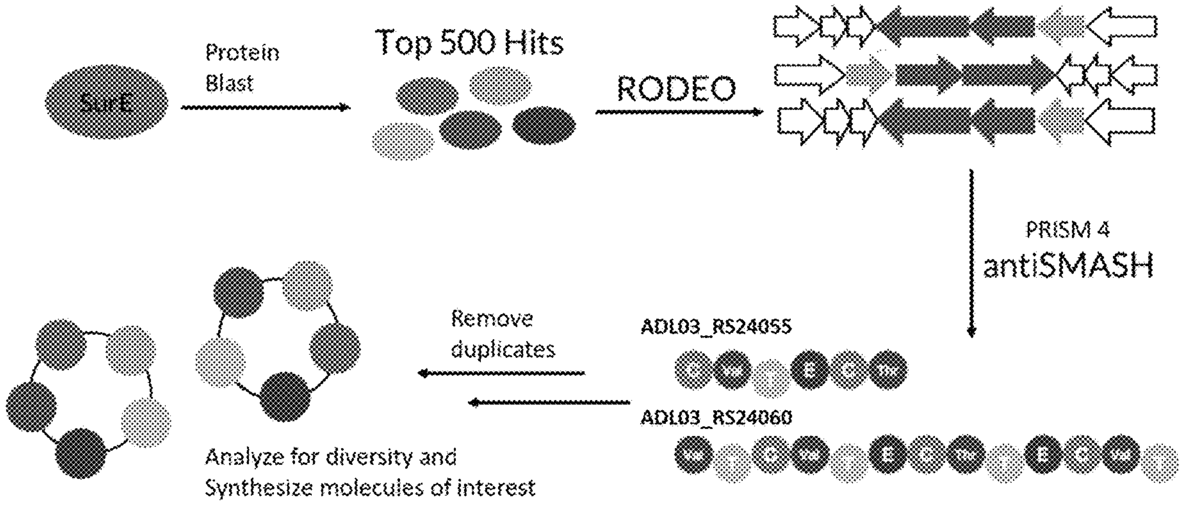
FIG. 1 outlines the method of SNaPP (Synthetic Natural Product Inspired Peptides).

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Unless defined otherwise, all technical and scientific terms used herein have the same meaning as commonly understood to one of ordinary skill in the art. As defined herein, the following terms and phrases shall have the meanings set forth below.

In the present disclosure the term "about" can allow for a degree of variability in a value or range, for example, within 10%, within 5%, or within 1% of a stated value or of a stated limit of a range. In the present disclosure the term "substantially" can allow for a degree of variability in a value or range, for example, within 90%, within 95%, 99%, 99.5%, 99.9%, 99.99%, or at least about 99.999% or more of a stated value or of a stated limit of a range.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated references should be considered supplementary to that of this document; for irreconcilable inconsistencies, the usage in this document controls.

The compounds described herein may contain one or more chiral centers or may otherwise be capable of existing as multiple stereoisomers. It is to be understood that in one embodiment, the invention described herein is not limited to any particular stereochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may include geometric centers, such as cis, trans, E, and Z double bonds. It is to be understood that in another embodiment, the invention described herein is not limited to any particular geometric isomer requirement, and that the compounds, and compositions, methods, uses, and medicaments that include them mar be pure, or may be any of a variety of geometric isomer mixtures. It is also to be understood that such mixtures of geometric isomers may include a single configuration at one or more double bonds, while including mixtures of geometry at one or more other double bonds.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

Pharmaceutically acceptable salts can be synthesized from the parent compound which contains a basic or acidic moiety by conventional chemical methods. In some instances, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, the disclosure of which is hereby incorporated by reference.

The term "solvate" means a compound, or a salt thereof, that further includes a stoichiometric or non-stoichiometric amount of solvent bound by non-covalent intermolecular forces. Where the solvent is water, the solvate is a hydrate.

The term "prodrug" means a derivative of a compound that can hydrolyze, oxidize, or otherwise react under biological conditions (in vitro or in vivo) to provide an active compound, particularly a compound of the invention. Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Specific prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers GmbH).

Further, in each of the foregoing and following embodiments, it is to be understood that the formulae include and represent not only all pharmaceutically acceptable salts of the compounds, but also include any and all hydrates and/or solvates of the compound formulae or salts thereof. It is to be appreciated that certain functional groups, such as the hydroxy, amino, and like groups form complexes and/or coordination compounds with water and/or various solvents, in the various physical forms of the compounds. Accordingly, the above formulae are to be understood to include and represent those various hydrates and/or solvates. In each of the foregoing and following embodiments, it is also to be understood that the formulae include and represent each possible isomer, such as stereoisomers and geometric isomers, both individually and in any and all possible mixtures. In each of the foregoing and following embodiments, it is also to be understood that the formulae include and represent any and all crystalline forms, partially crystalline forms, and non-crystalline and/or amorphous forms of the compounds.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As used herein, the term "administering" includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically acceptable carriers, adjuvants, and vehicles.

Illustrative formats for oral administration include tablets, capsules, elixirs, syrups, and the like. Illustrative routes for parenteral administration include intravenous, intraarterial, intraperitoneal, epidural, intraurethral, intrasternal, intramuscular and subcutaneous, as well as any other art recognized route of parenteral administration.

Illustrative means of parenteral administration include needle (including microneedle) injectors, needle-free injectors and infusion techniques, as well as any other means of parenteral administration recognized in the art. Parenteral formulations are typically aqueous solutions which may contain excipients such as salts, carbohydrates and buffering agents (preferably at, a pH in the range from about 3 to about 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art. Parenteral administration of a compound is illustratively performed in the form of saline solutions or with the compound incorporated into liposomes. In cases where the compound in itself is not sufficiently soluble to be dissolved, a solubilizer such as ethanol can be applied.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient, will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

Depending upon the route of administration, a wide range of permissible dosages are contemplated herein, including doses falling in the range from about 1 μg/kg to about 1 g/kg. The dosages may be single or divided, and may administered according to a wide variety of protocols, including q.d. (once a day), b.i.d. (twice a day), t.i.d. (three times a day), or even every other day, once a week, once a month, once a quarter, and the like. In each of these cases it is understood that the therapeutically effective amounts described herein correspond to the instance of administration, or alternatively to the total daily, weekly, month, or quarterly dose, as determined by the dosing protocol.

In addition to the illustrative dosages and dosing protocols described herein, it is to be understood that an effective amount of any one or a mixture of the compounds described herein can be determined by the attending diagnostician or physician by the use of known techniques and/or by observing results obtained under analogous circumstances. In determining the effective amount or dose, a number of factors are considered by the attending diagnostician or physician, including, but not, limited to the species of mammal, including human, its size, age, and general health, the specific disease or disorder involved, the degree of or involvement or the severity of the disease or disorder, the response of the individual patient, the particular compound administered, the mode of administration, the bioavailability characteristics of the preparation administered, the dose regimen selected, the use of concomitant medication, and other relevant circumstances.

The term "patient" includes human and non-human animals such as companion animals (dogs and cats and the like) and livestock animals. Livestock animals are animals raised for food production. The patient to be treated is preferably a mammal, in particular a human being.

In some illustrative embodiments, this disclosure relates to a method for discovery of bioactive molecules comprising the steps of a. predicting the sequences and structures of bioactive molecules based on a non-ribosomal peptide synthetase using a bioinformatics tool;
b. screening of those predicted sequences and structures to afford a set of molecules with novelty and uniqueness;
c. synthesizing chemically those novel and unique molecules;
d. further screening of those chemically synthesized molecules in one or more bioassays; and
e. identifying and confirming bioactive molecules based on the results of said bioassays.

In some illustrative embodiments, this disclosure relates to a method for discovery of bioactive molecules as disclosed herein, wherein said non-ribosomal peptide synthetase is a reductase domain.

In some illustrative embodiments, this disclosure relates to a method for discovery of bioactive molecules as disclosed herein, wherein said non-ribosomal peptide synthetase is in a biosynthetic gene cluster with a penicillin binding protein-like cyclase.

In some illustrative embodiments, this disclosure relates to a method for discovery of bioactive molecules as disclosed herein, wherein said bioactive molecules are a peptide.

In some illustrative embodiments, this disclosure relates to a method for discovery of bioactive molecules as disclosed herein, wherein said bioactive molecules are a cyclic head-to-tail cyclized peptide.

In some illustrative embodiments, this disclosure relates to a method for discovery of bioactive molecules as disclosed herein, wherein said bioactive molecules are a peptide molecule comprising one or more non-natural amino acid moieties.

In some illustrative embodiments, this disclosure relates to a method for discovery of bioactive molecules as disclosed herein, wherein said peptide comprises four to eleven amino acid residues.

In some illustrative embodiments, this disclosure relates to a method for discovery of bioactive molecules as disclosed herein, wherein said bioactive molecules are:

-continued pNP-111

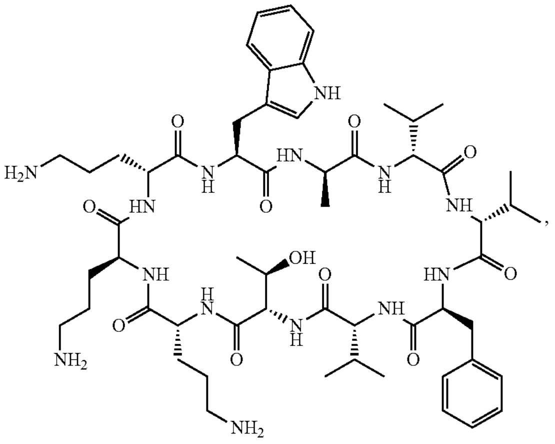

pNP-80

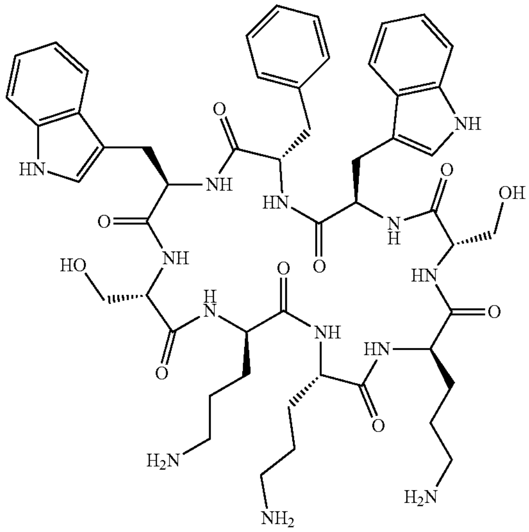

pNP-66

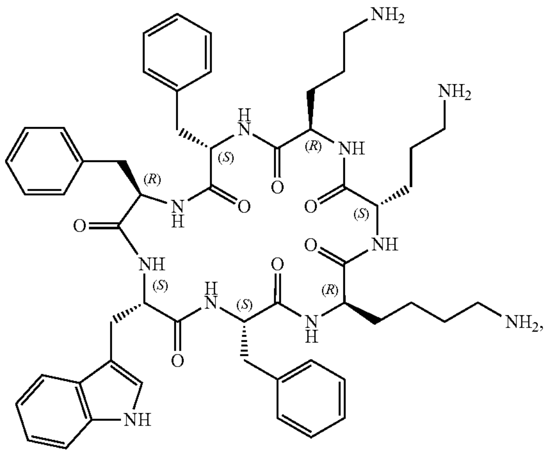

CS-1-07 pNP-51

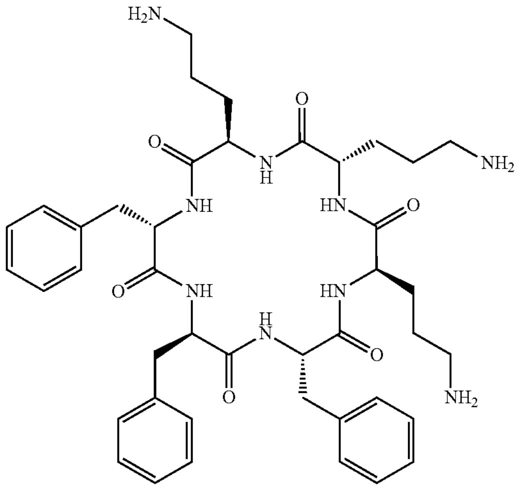

pNP-23

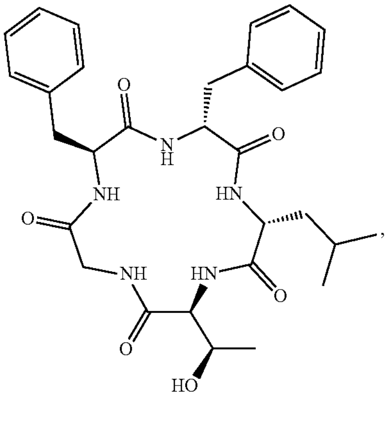

-continued pNP-43

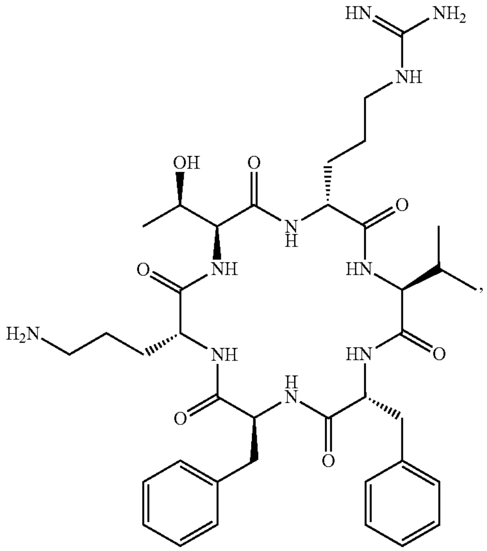

, and pNP-40

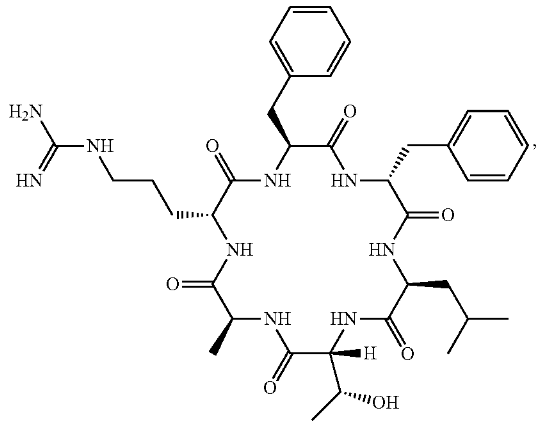

, or a pharmaceutically acceptable salt thereof.

In some illustrative embodiments, this disclosure relates to a method for discovery of bioactive molecules as disclosed herein, wherein said bioactive molecules are antibiotics.

In some illustrative embodiments, this disclosure relates to a method for discovery of bioactive molecules as disclosed herein, wherein said bioinformatics tools comprises PRISM and antiSMASH.

In some illustrative embodiments, this disclosure relates to a method for discovery of bioactive molecules as disclosed herein, wherein said method is a unique combination of techniques of bioinformatics and chemical synthesis for identification of bioactive peptide molecules.

In some illustrative embodiments, this disclosure relates to a pharmaceutical composition comprising one or more of the following compounds together with one or more pharmaceutically acceptable diluents, excipients, or carriers:

pNP-80

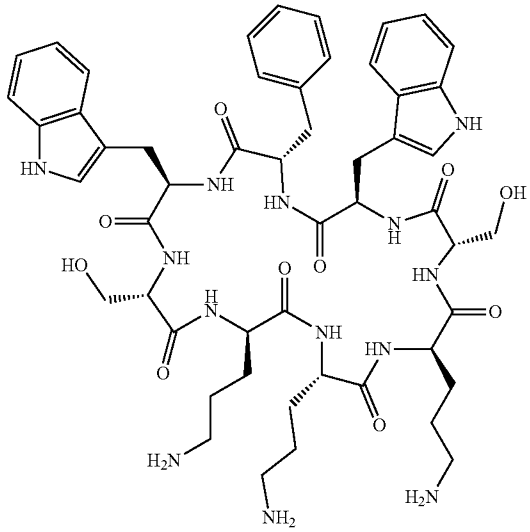

pNP-51

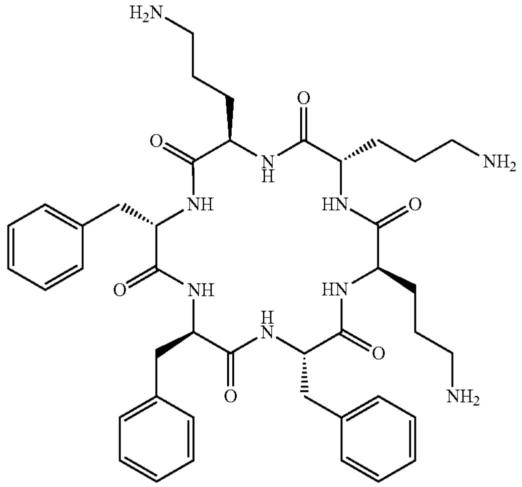

pNP-111

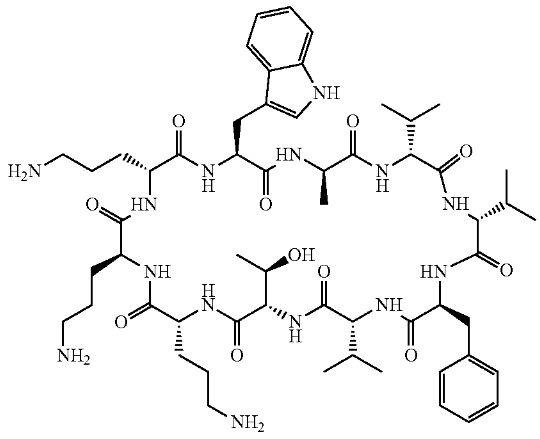

,

-continued pNP-66

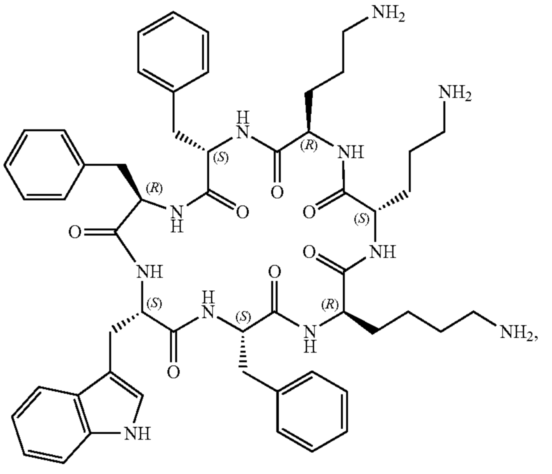

CS-1-07 pNP-23

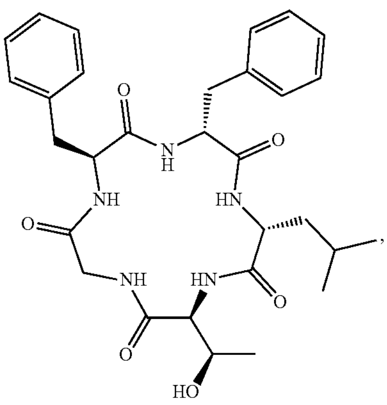

pNP-43

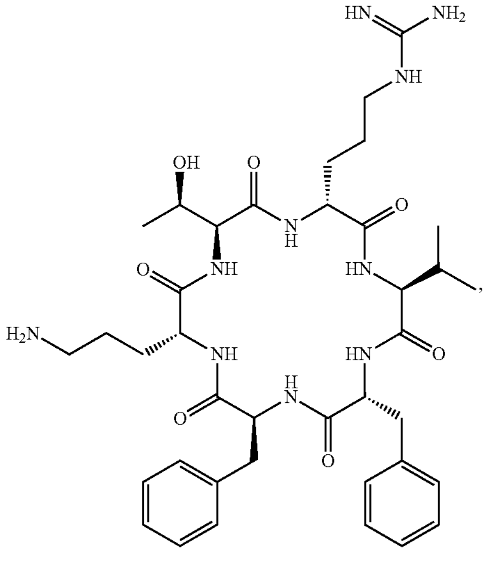

and

-continued pNP-40

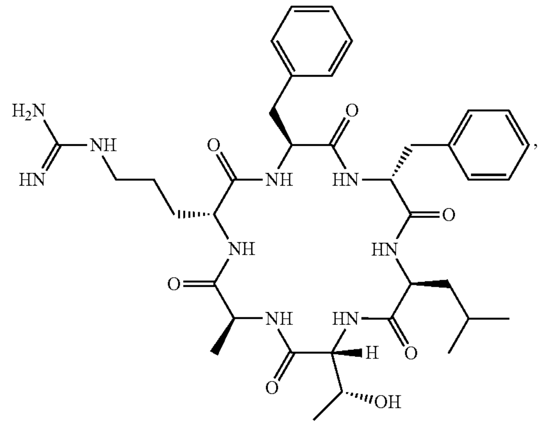

or a pharmaceutically acceptable salt thereof.

The following non-limiting exemplary embodiments are included herein to further illustrate the invention. These exemplary embodiments are not intended and should not be interpreted to limit the scope of the invention in any way. It is also to be understood that numerous variations of these exemplary embodiments are contemplated herein.

Traditionally, novel NRPs have been discovered by a classical fermentation approach[12] whereby crude bacterial extracts are screened for biological activity. While this approach has been extremely successful, it is very time consuming. The process of going from a bioactive extract to a completely elucidated structure takes minimally several months and oftentimes over a year. Additionally, each new NP requires optimization of fermentation conditions and purification sequences, thus preventing easy automation of the process. Rediscovery of known NPs is also a major limitation.[13] Recent advances in whole-genome sequencing and bioinformatics have revealed a vast number of NRPS biosynthetic gene clusters (BGCs) for which no known NP can be attributed.[14] Harnessing the full biosynthetic potential of these organisms is complicated by the fact that a small fraction (~2%) of bacteria are culturable in the laboratory[2,15] and many BGCs are transcriptionally inactive (cryptic) under standard laboratory conditions.[14] Access to the NPs produced via these BGCs often requires heterologous expression or promoter optimization, both of which are very time consuming and frequently unsuccessful.

We hypothesized that we could overcome these difficulties by developing SNaPP (Synthetic Natural Product Inspired Peptides, FIG. 1), a method that combines bioinformatics with chemical synthesis. Specifically, the method utilizes 1) bioinformatics tools such as antiSMASH[16] and PRISM[17] to predict peptide products formed by NRPS BGCs identified in bacterial genomes and 2) chemical synthesis to access the predicted peptides. This synthesis-first approach has many advantages over traditional fermentation approaches: 1) This approach skips bacterial culture and the need for fermentation optimization, 2) It avoids rediscovery of known NPs by comparison with known BGCs, 3) Products from cryptic BGCs or currently unculturable bacteria can easily be accessed, and 4) Each part of SNaPP from the identification of the BGCs to NP predictions to chemical synthesis is scalable and easily automated, greatly expediting the process.

Others have previously prepared predicted NRPs by solid-phase peptide synthesis and were successful in the discovery of several biologically active compounds.[18-22] However, few of these reports has explored the synthesis of predicted cyclic NRPs,[22,23] despite the fact that nearly 67% of known NRPs possess a cyclic motif.[24,25] One reason for this observation may be the limited ability of bioinformatics programs to predict how NRPs cyclize. The thioesterase (TE) domain is typically the terminal module of an NRPS and is often responsible for peptide cyclization.[26] However, TE domains catalyze the production of multiple cyclic motifs including lactams and lactones in head-to-tail or sidechain-to-tail form.[27,28] Others have overcome this by synthesizing all the potential cyclic structures.[22,23] This comprehensive approach is impressive and resulted in a very good antibiotic hit rate (15/157, ~10%). 23 However, it requires synthesis of multiple compounds per BGC, greatly increasing the time and reagents necessary make these molecules. Additionally, it greatly increases the number of compounds needed to be screened. One of the major advantages of prioritizing NRPs is their increased likelihood of having bioactivity compared to a random cyclic peptide.[29] It is highly unlikely that the incorrectly cyclized structures will have activity due to the large effect that cyclization site has on three-dimensional shape of molecules. Therefore, a strategy that does not prioritize the correct cyclization site is hypothesized to be less efficient than one that targets only the molecules with the natural cyclization site.

Interestingly, numerous NRPS BGCs do not contain a thioesterase domain and instead are thought to be released from the NRPS via stand-alone enzymes. Recently, the penicillin binding protein (PBP)-like cyclases have been identified as a novel class of stand-alone NRPS cyclases.[30-32] PBP-like cyclases have thus far only been found to catalyze cyclization of the C-terminus with the N-terminus to furnish head-to-tail cyclic lactams. Herein, we describe a new method SNaPP (Synthetic Natural Product Inspired Peptides), which expedites discovery of novel bioactive cyclic peptides via the synthesis of predicted NPs (pNPs). SNaPP prioritizes head-to-tail cyclic peptides by focusing on NRPS BGCs containing PBP-like cyclases. While these peptides are not intended to be the true NPs, we expect to bias ourselves toward head-to-tail cyclic peptides with very similar structures and bioactivities to the true NPs.

Results and Discussion

Identification of pNPs. SurE, the PBP-like cyclase that catalyzes the cyclization of the surugamides, is one of the most well studied PBP-like cyclases.[30-33] surE along with the genes encoding the PBP-like cyclases for the head-to-tail cyclized peptide NPs ulleungmycin (ulm16), desotamide B (dsaJ), the mannopeptimycins (mppK), the pentaminomycins (penA), the noursamycins (nsm16), and the curacomycins (KUM80512.1) are all found in close proximity to the NRPS that produces the peptide NP.[31,34-36] This co-localization suggests that the genes for these cyclases could be used as a genetic handle for identifying other cyclic head-to-tail NRPs. Our strategy is outlined in FIG. 1. We have chosen to focus exclusively on head-to-tail cyclic peptides because all PBP-cyclase containing BGCs analyzed to date encode for the production of head-to-tail cyclic peptides. However, a limitation of this strategy is that the PBP-like cyclases are a relatively new class of enzymes. It is possible that some PBP-like cyclases perform alternative cyclizations (e.g. sidechain-to-head), and we just have not yet discovered them.

Figure 2A:
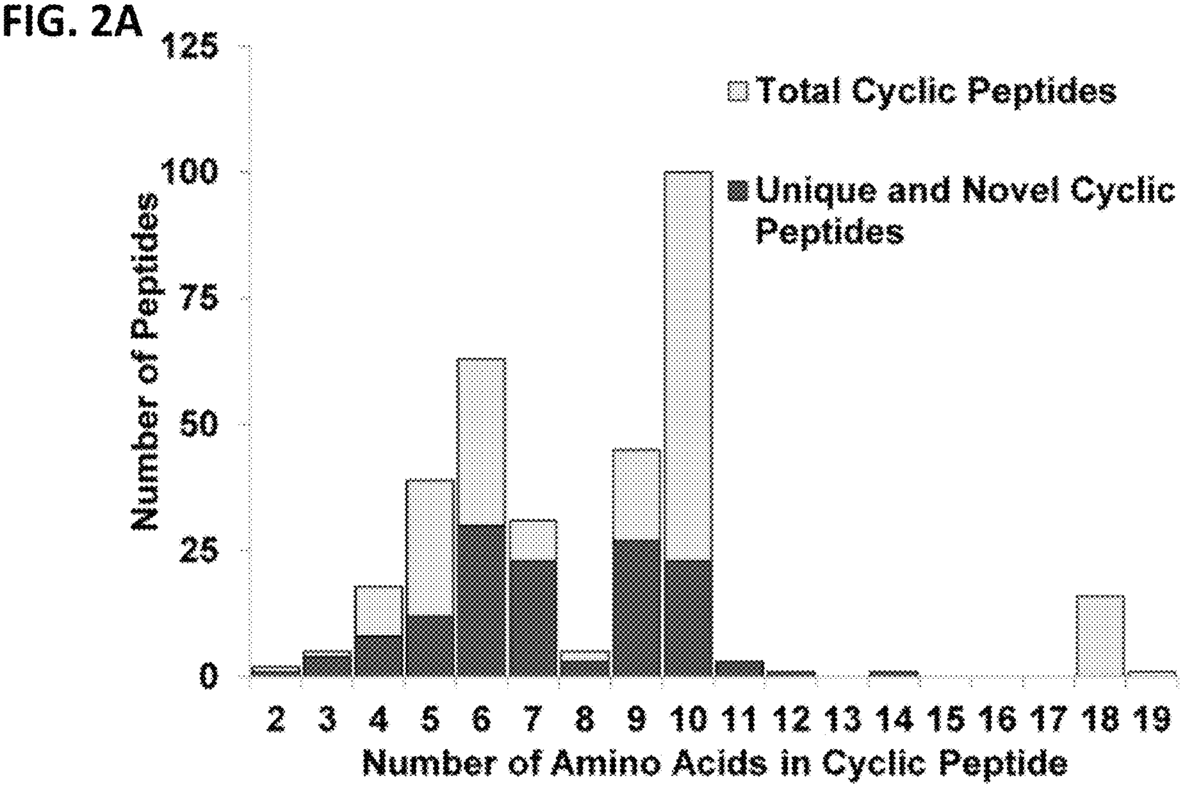
FIGS. 2A-2D show the diversity of pNPs.

First, a BlastP[37] search for SurE was performed and the top 500 hits were analyzed further. The genetic neighborhood for these hits was identified using RODEO.[38] 396 (79%) of the BGCs had NRPS genes 10 genes or less away. Clusters at the end of a contig or with incomplete records in NCBI (80, ~20%) were removed prior to further analysis. The remaining 316 NRPS containing BGCs were then analyzed using bioinformatics softwares including PRISM 4[17] and antiSMASH 5.0[16] to predict the structure of the NRPs (See Appendix materials). Generally, predictions between the two programs agreed well. Tanimoto analysis of the predictions from PRISM 4 or antiSMASH 5.0 for the 5 known molecules within our dataset compared to their actual structures suggested similar accuracies (Supplementary FIG. 1A). Additionally, their predictions for uncharacterized BGCs also were similar (Supplementary FIG. 1B). We ultimately chose to use the PRISM predictions as the basis for our studies for two major reasons. First, and most importantly, other studies have found that PRISM is better at predicting known NPs compared to antiSMASH when the dataset it larger than the knowns that we have in our dataset.[39] Specifically, the structures predicted by PRISM 4 and antiSMASH 5.0 for 753 BGCs that encoded known NPs were previously analyzed for their similarity to the known structure. PRISM 4 significantly outperformed antiSMASH 5.0.[39] Second, PRISM is more likely to give a structural prediction.[39] When 3759 bacterial genomes were previously analyzed, PRISM was able to predict structures for 3078 NRPS while antiSMASH 5.0 was able to predict structure for 2779 NRPS.[39]. Using PRISM, 140 unique cyclic peptides were identified. Nine of the peptides were previously known NRPs (mannopeptimycin, desotamide B, ulleungmycin, and 6 copies of the surugamide cluster) leaving 131 unique and novel cyclic peptides of varying sizes to explore further (FIG. 2A).

Previously, Jacques and co-workers found that NRPs vary in size between 2 and 23 amino acids with the most frequent sizes of NRPs being between 7 and 9 amino acids.[40] While we see many peptides with 7 and 9 amino acids, we see very few with 8 amino acids and instead see a large number of 6 and 10. Additionally, the unnatural amino acid ornithine is predicted much more often than expected. Based on the number of occurrences in the Norine database,[24] we would expect ~8% of NRPs to contain ornithine. We found that ~70% of our pNPs contain ornithine. It is unclear whether this is due to the prediction software or if ornithine is truly overrepresented in this set of peptides. Interestingly, antiSMASH often predicted glutamine when PRISM predicted ornithine. Another common difference was that antiSMASH would often predict tyrosine when PRISM predicted tryptophan. Given the structural similarity of these amino acids, we were not surprised by these differences.

Figure 2B:
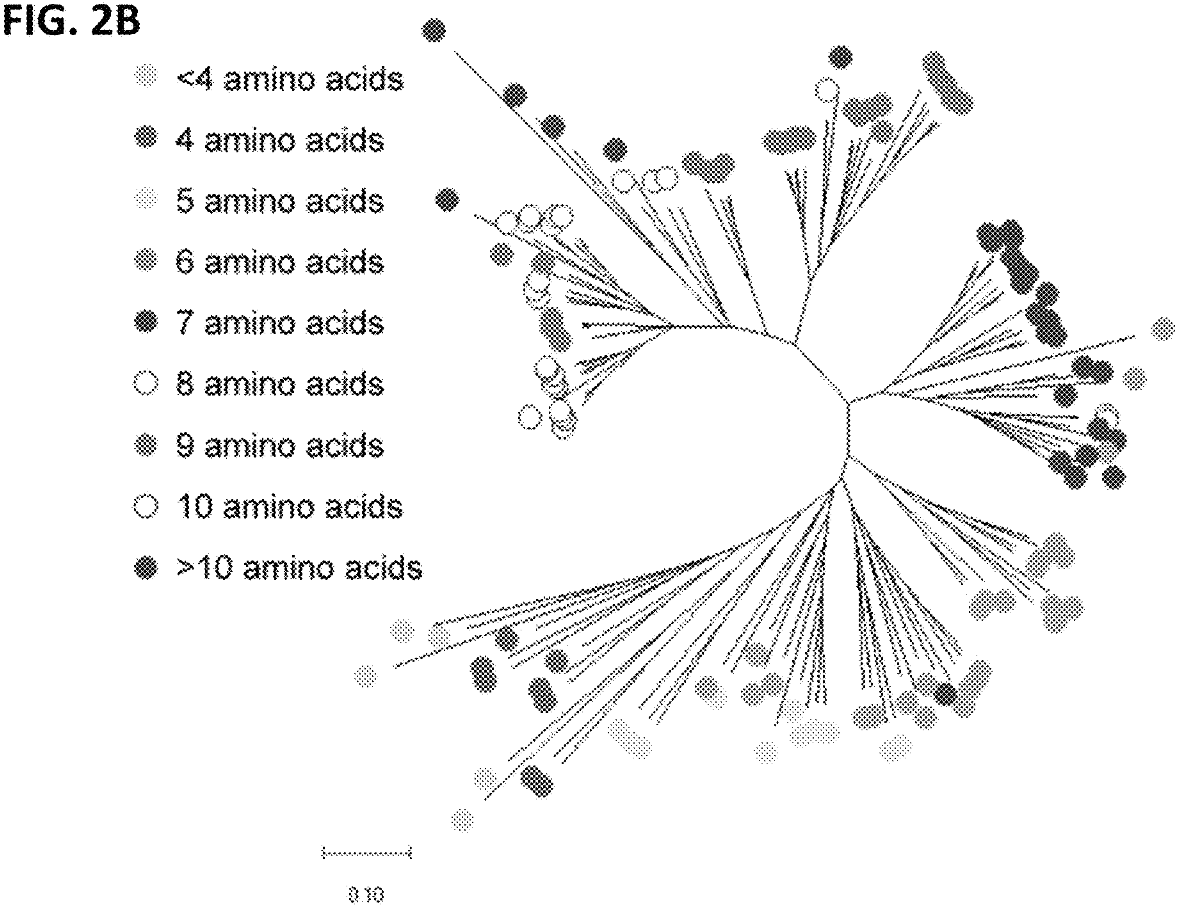

Diversity of pNPs. Because the structures of molecules determine their functions, structural diversity is essential for any compound library that will be used for bioactivity screening.[41] To assess the diversity of the pNPs and determine the best molecules to synthesize for testing, we first used ChemMine Tools[42] to calculate the Tanimoto coefficients for the novel molecules identified. The Tanimoto coefficients were then used to generate both a heatmap as well as a tree (FIG. 2B and FIG. S2A). Peptides of the same size generally cluster together while still having noticeable structural differences.

Figure 2C:
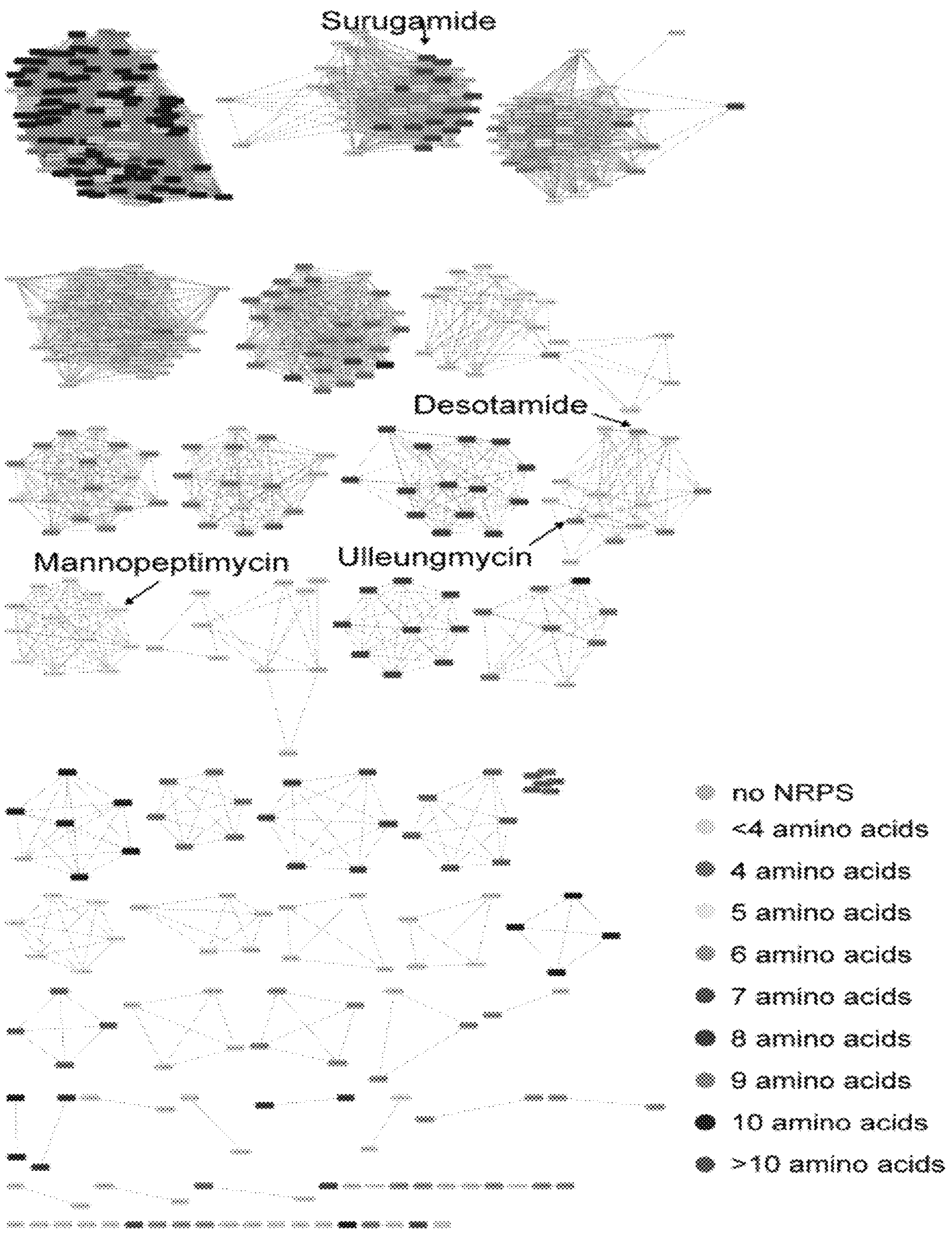

Bioinformatics methods were also employed to analyze the diversity of the library. A sequence similarity network (SSN)[43] of the PBP-like cyclases was generated. The PBP-like cyclases tend to cluster based on the size of their corresponding NRPs, suggesting that PBP-like cyclases might be specific for certain ring sizes (FIG. 2C and FIG.

Figure 2D:
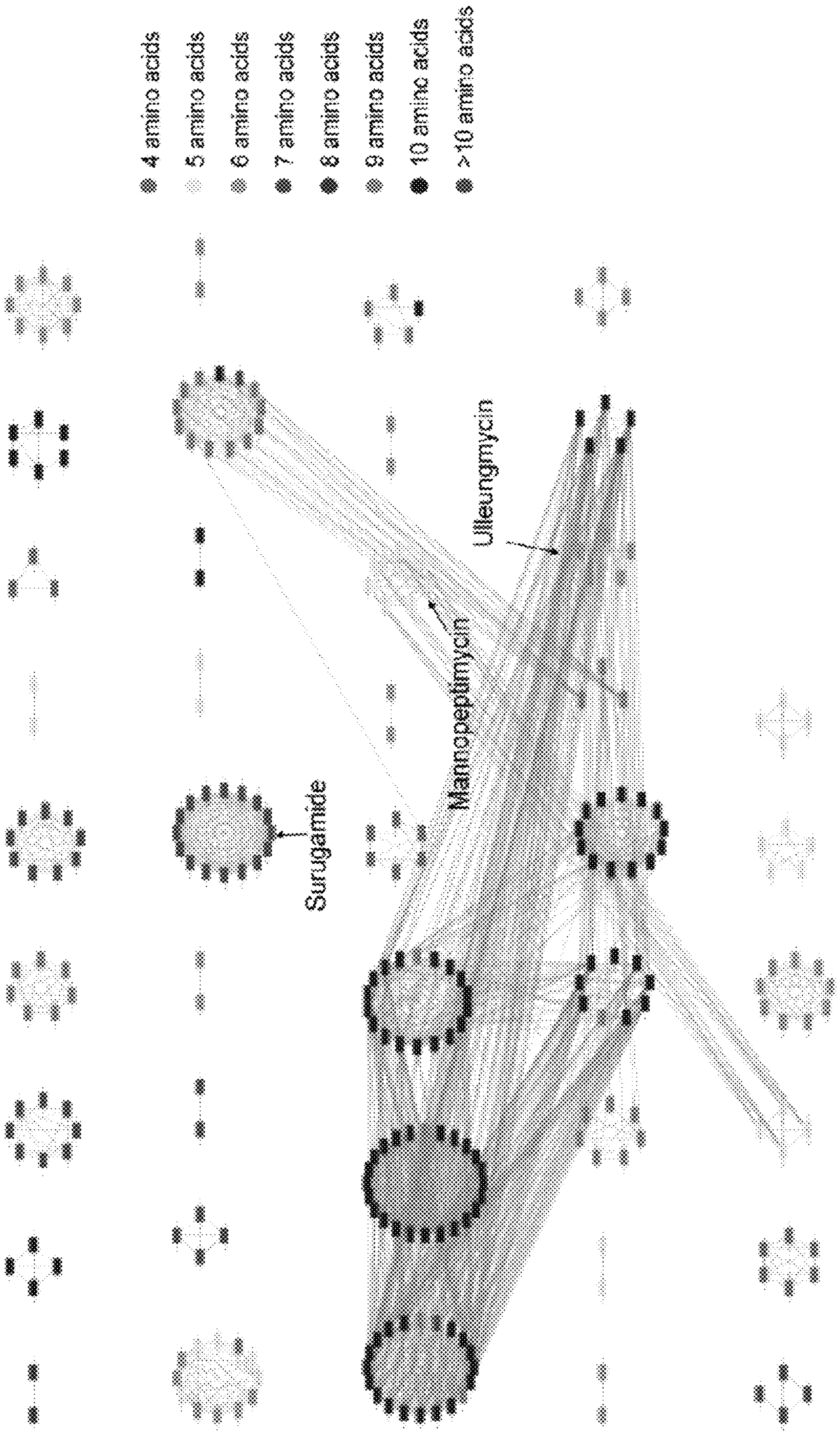

S3). Interestingly, occasionally different sizes are predicted within the same cluster, suggesting that either these cyclases are more flexible or potentially that the NRPS next to the aberrant cyclase may act in an iterative fashion. We also performed BiGSCAPE analysis[44] on the BGCs containing the PBP-like cyclases and NRPS genes (FIG. 2D and FIG. S4). This analysis revealed 86 NRPS families with an average of 4 BGCs per family. This data, in agreement with the Tanimoto data, confirmed a varied set of structures and helped us to design a diverse library.

Synthesis of a diverse pNP library. 51 chemically diverse pNPs were chosen for synthesis (see FIG. S2-4). Specifically, molecules from distinct branches on the Tanimoto tree were chosen. These were further narrowed down based by choosing molecules from a variety SSN clusters and BigSCAPE families with a particular emphasis on molecules not from clusters or families with previously known molecules. Challenging to access amino acids such as protected enduracididine and hydroxyphenylglycine were replaced with the structurally similar amino acids arginine and phenylglycine, respectively. Linear sequences were prepared using standard solid-phase peptide synthesis (SPPS) followed by solution-phase cyclization, deprotection, and purification (FIG. S5).45, 46 The entire sequence from pNP prediction through purification can be completed in 7 days in a straightforward way. Additionally, all steps except HPLC purification can easily be accomplished in parallel. Growth of a NP producing organism often takes longer than this, with fermentation optimization, purification, and structure validation regularly exceeding a year. Thus the SNaPP process clearly expedites the process greatly compared to traditional fermentation.

Bioactivity testing. Initial compounds were tested for activity against antibiotic sensitive and antibiotic resistant ESKAPE pathogens at concentrations varying between 0.5 and 32 μg/mL using the CLSI microbroth dilution assay.[47] Any well with greater than 90% death was considered a hit. Overall, 14 hits (MIC ≤32 μg/mL) were observed with 4 against Gram-negative organisms (FIG. 3), 9 of them being against Gram-positive organisms (FIG. S6) and, and 1 hit against both. This is a very promising hit rate (~30%), especially when compared to other antibiotic discovery programs, which have struggled to find any hits, especially against Gram-negative organisms.[48,49] It also is approximately 3-fold more efficient compared to previous syn-BNP approaches that did not prioritize correctly cyclized structures.[23] An Alamar blue viability assay revealed that these molecules are non-toxic to the A549 non-small cell lung cancer cell line, suggesting they likely have good selectivity for bacterial cells over mammalian cells. (FIGS. 3 and S6) Additionally, hemolysis assays with human blood revealed that many also had no hemolytic effects at concentrations up to 53 μg/mL (FIGS. 3 and S6), providing strong evidence that they are promising antibiotic leads.

Figure 4A:
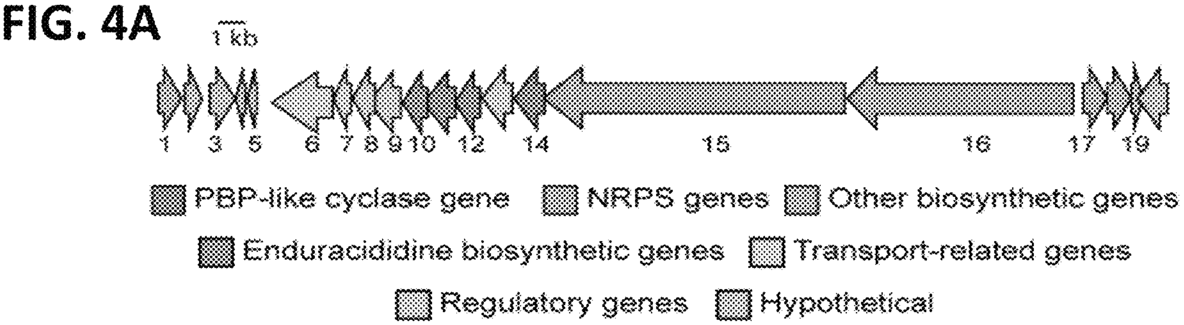
FIGS. 4A-4B. BGC for pNP-43.
Figure 4B:
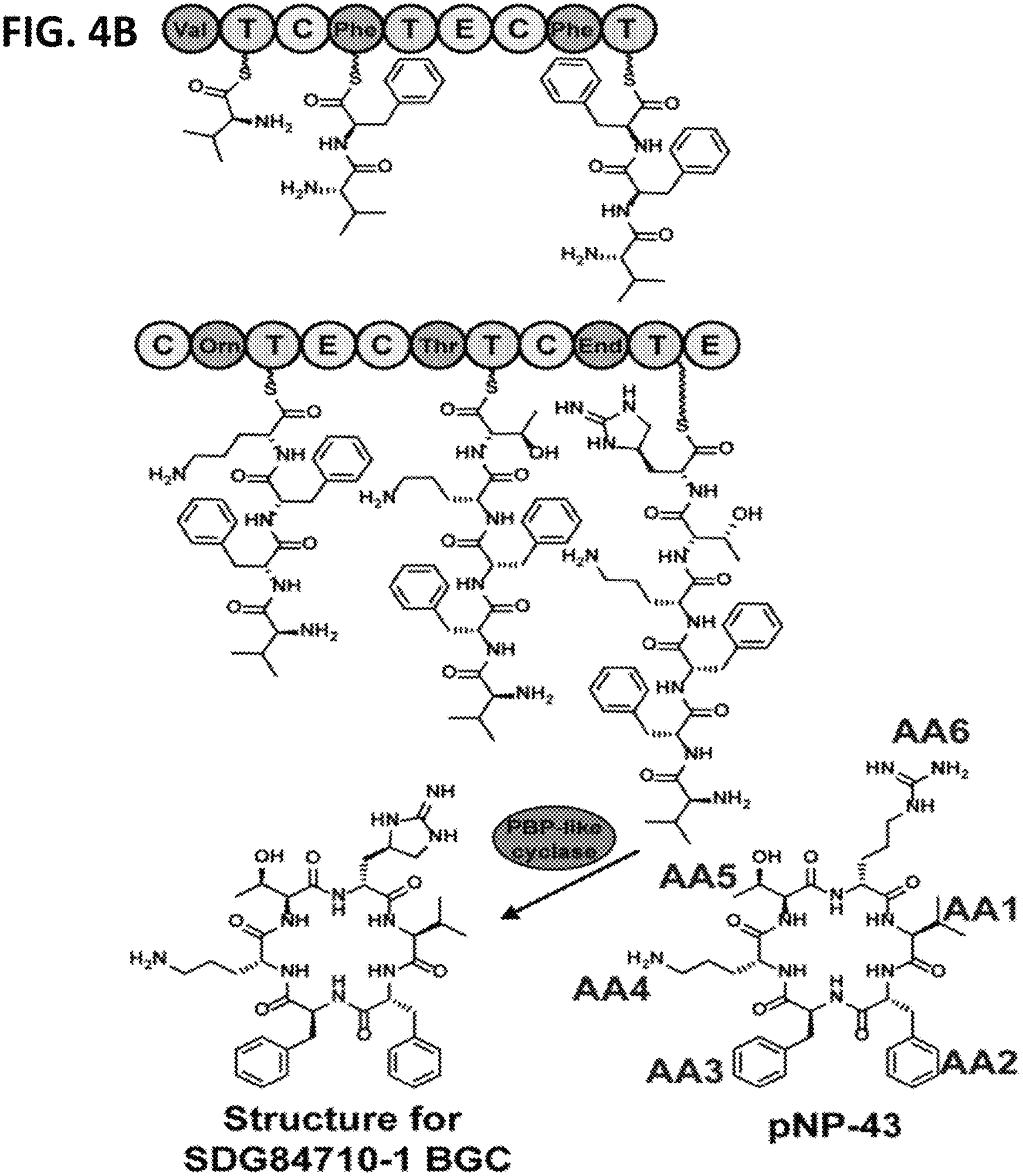
Figure 5A:
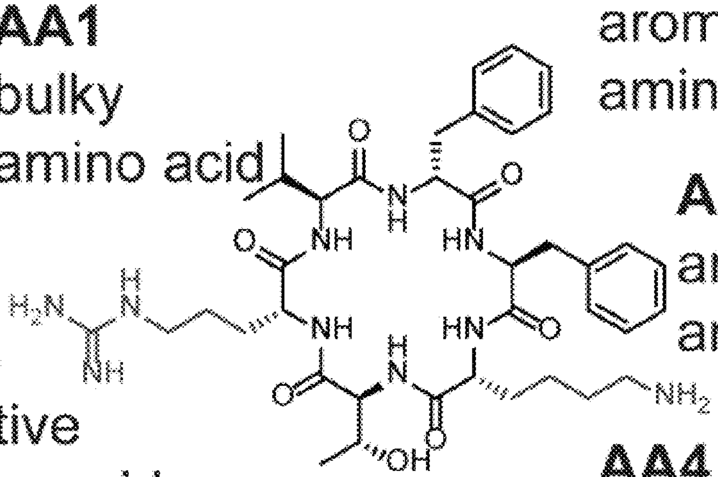
FIGS. 5A-5B. Mechanism of action studies.

Derivative development and mechanism of action studies. Based on the results described above, we chose to explore derivatives of pNP-43, a compound with activity against several Gram-negative bacteria and no observed hemolytic activity or mammalian cell toxicity. pNP-43 is predicted to be produced by *Lechevalieria fradiae* CGMCC 4.3506, a strain originally isolated from the Wutaishan Mountain in the Shanxi province of China. In addition to the PBP-like cyclase and NRPS genes, the BGC contains genes with high similarity to the enduracididine biosynthetic genes, providing strong support that enduracididine is incorporated into this cyclic peptide (FIG. 4 and Table S2). Structure predictions by PRISM further support this with adenylation domain 6 predicted to load enduracididine. Due to challenges in obtaining enduracididine, we chose to substitute enduracididine for the next highest prediction, arginine. While enduracididine is often important for the bioactivity of natural products (e.g. teixobactin), others have shown that replacement of enduracididine with arginine often results in a molecule that retains bioactivity.[50-52] However, at least in the case of teixobactin, this substitution does result in an approximate 10-fold decrease in potency. When developing derivatives, the arginine was exchanged with amino acids having similar chemical structures including lysine, ornithine, and 2,4-diaminobutyric acid (pNP-43a-c, FIG. S7). However, the parent molecule was the most active (Table S2). After further examination of the predictions by antiSMASH 16 and PRISM[17] (Table S3), we chose to develop other derivatives by modifying the amino acid at position 4 (Orn). While ornithine is the number one prediction for amino acid 4, arginine and lysine also scored well thus we chose to incorporate these residues into our derivatives (pNP-43d-e in FIG. S6B). Substituting lysine in place of ornithine at position 4 (pNP-43d) resulted in biological activity that was 2-fold more potent against antibiotic resistant *A. baumannii* compared to the initial molecule. We then performed an alanine scan on pNP-43d to determine the amino acids that were necessary for activity. Substitution of each amino acid except for threonine resulted in inactive molecules, suggesting that all amino acids except amino acid 5 are essential for activity. Finally, we explored other substitutions at position 6. Derivatives that substituted this position with histidine, tryptophan, asparagine, or glutamine were all inactive, suggesting that amino acid position 6 must be a basic amino acid. Further derivatives helped us to establish a structure activity relationship (FIGS. 5A and S7). Additionally, the linear version of pNP-43d (pNP-43r) was completely inactive (MIC>128 ug/mL), confirming the importance of cyclizing the peptides.

Figure 5B:
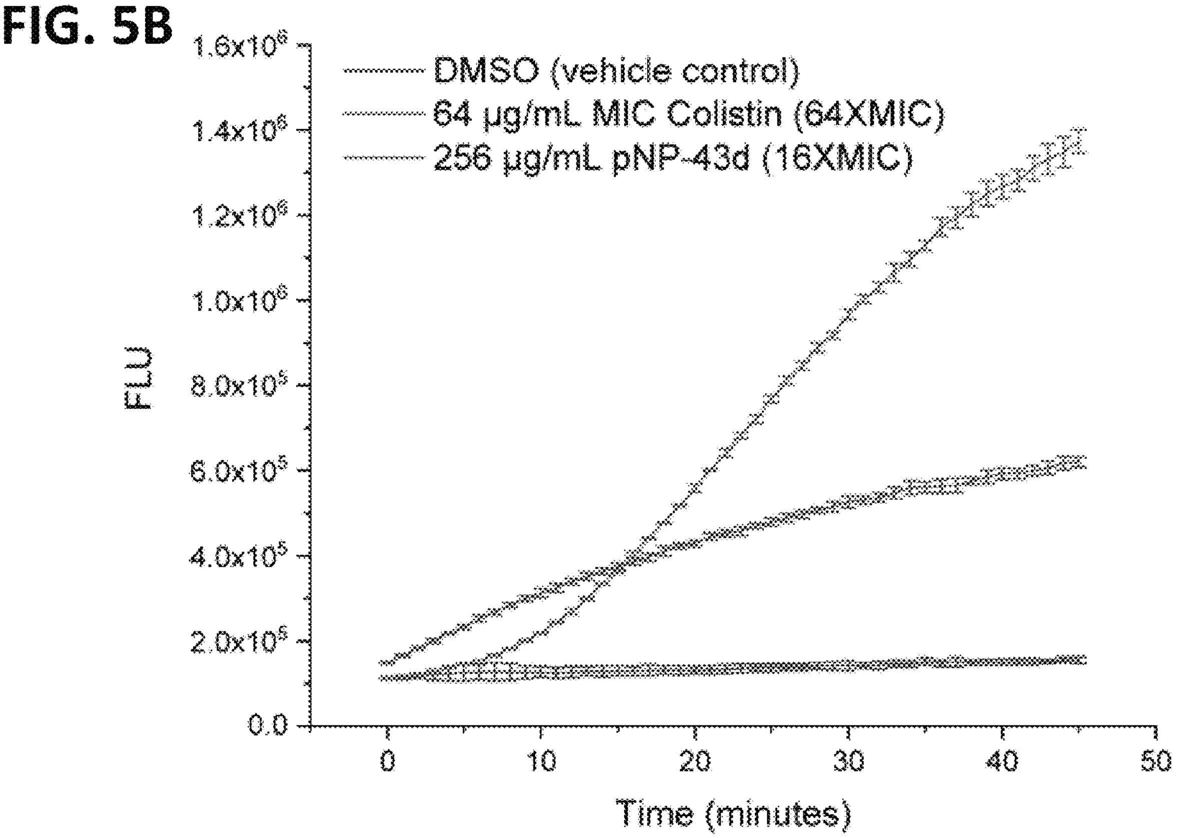

Due to the improved activity of pNP-43d against the antibiotic resistant *A. baumannii*, we chose to study its mechanism of action. Many cyclic peptides are known to cause bacterial cell lysis. This is particularly true of cationic peptides such as the polymixins.[53] Specifically, colistin (i.e. polymixin E) is known to interact with Lipid A via its 5 positively charged amino acids, displace divalent cations, and weaken the bacterial outer membrane of Gram-negative bacteria.[54] This ultimately allows the peptide to enter the cell, where its additional activities have been postulated to cause cell death. The success of cationic peptides as Gram-Negative antibiotics is so well precedented that others have even used it as a strategy to find novel antibiotics such as non-ribosomal peptides asbrevicidine and laterocidine, each of which has three basic residues.[53] Because pNP-43 derivatives require basic amino acids at positions 4 and 6 for activity and because they only show activity against Gram-negative bacteria, it is possible that it is acts similarly to colistin and other cationic peptides. Specifically, it may utilize its positively charged amino acids to interact with the outer membrane and then induce bacterial cell lysis. Colistin-resistant bacteria are also resistant to pNP-43 and pNP-43d. The fact that these molecules are active against antibiotic resistant strains that are sensitive to colistin but not those that are resistant suggests that it may be acting similarly. To further explore this hypothesis, we tested pNP-43d for its ability to lyse bacterial cells using a previously reported Sytox green assay.[55] pNP-43d clearly resulted in bacterial cell lysis at concentrations varying from 2 to 16 times the MIC for both wild type and antibiotic resistant *A. baumannii* (FIG. 5B and FIG. S8). Based on these combined results, pNP-43d appears to have a similar mechanism of action to colistin.

Conclusions

Described herein is the development of SNaPP, a method to greatly expedite the discovery of bioactive molecules inspired by NPs. Cyclic peptides were chosen as an initial target due to their history as important sources of medicines along with the established bioinformatics approaches for predicting the peptide sequences. Head-to-tail peptides were targeted by identifying NRPS BGCs that co-occur with genes from a recently discovered family of stand-alone cyclases, the PBP-like cyclases, which to date have only been found in BGCs for head-to-tail cyclic peptides. This approach allowed for identification of 131 unique and novel cyclic peptides. 51 diverse pNPs were chemically synthesized and tested for antibiotic activity. Approximately 30% of pNPs had activity with several showing very promising activity against difficult-to-treat Gram-negative bacteria. As prediction softwares for NP BGCs improve, this strategy will only increase in its utility. Overall, SNaPP is a powerful method for the rapid identification of biologically inspired lead molecules.

As disclosed herein, other types of non-ribosomal peptide synthetases, such as reductase domains, may also benefit from the instant disclosed technologies.

Materials and Methods

General Information. Solvents were purchased from Fisher Scientific and used without further purification. Fmoc amino acids, coupling reagents, were purchased from Chem-Impex International. 2-CTC resin was purchased from ChemPep Incorporated. All other reagents were purchased from commercially available sources (Sigma Aldrich, Acros Organics, Oakwood Chemical, TCI Chemicals), and used without further purification. See Key Resources Table for more information.

Bacterial Strains. All strains used in this study except the *Bacillus* strain and the colistin resistant *E. coli* strains were obtained from Professor Paul Hergenrother (UIUC). The *Bacillus* strain was obtained from Professor William Metcalf (UIUC). The colistin resistant *E. coli* strains (AR Bank Number 0346, 0349, and 0350) were obtained from the CDC AR Isolate bank). *E. coli* ATCC 25922 (wild type, WT) BAA-2469 (resistant, R), colistin resistant *E. coli, K. pneumonia* ATCC 27736 (WT) and BAA-2146 (R), *A. baumannii* ATCC 19606 (WT) and KB349 (R), and *P. aeruginosa* PAO1 (WT) and PA1000 (R) were grown on Mueller Hinton Broth 2 (Sigma Aldrich). *S. aureus* ATCC 29213 (WT) and NRS3 (R), *Enterococcus* species ATCC 19433 (WT) and S235 (R), and *B. subtilis* 6633 (WT) were maintained on Bacto Brain Heart Infusion.

Prediction of cyclic peptide structure. The accession numbers for the top 500 hits from the SurE BlastP were downloaded and used as the input for RODEO 1. Biosynthetic gene clusters were then manually analyzed for the presence of non-ribosomal peptide synthetase (NRPS) genes. If an NRPS was at the end of a contig, the cluster was not considered further. If the NRPS was not at the end of the contig, the FASTA file for the cluster was then analyzed using both PRISM 4.0 2 and antiSMASH 5.0 3. Generally, both programs agreed well. Initial structures were assigned based on the PRISM results (see Supplementary Excel Document). Derivatives were designed based on results from both programs.

Tanimoto similarity analysis. Tanimoto similarity analysis was accomplished with ChemMine Tools 4 using the following parameters for hierarchical clustering: Display values: Z-scores; Linkage method: single; Heatmap: distance matrix.

Sequence similarity analysis. Sequence similarity analysis of the PBP-like cyclases was accomplished using the EFI-Enzyme Similarity Tool 5 and visualized using Cytoscape 3.6.1 6. An alignment score of 120 was used for generating the networks in this paper.

BiG-SCAPE analysis. BiG-SCAPE analysis7 was performed on the 316 BGCs containing both a PBP-like cyclase and an NRPS. The antiSMASH outputs from the prediction of the cyclic peptide structure were used an inputs for BiG-SCAPE. The output was visualized using Cytoscape 3.6.1.

General Procedure for Resin Loading. 2-Chlorotrityl chloride (2-CTC) resin (1.0 g, 0.77 mmol/g, 0.77 mmol, 100-200 mesh), was swelled in DMF for 30 min, drained, and treated with a solution of Fmoc-protected amino acid (2.3 mmol) and DIEA (537 μL, 3.09 mmol) in DMF (11 mL). The resulting mixture was gently agitated for 2 h, after which, the resin was filtered and washed with DMF (2×5 mL). Remaining unreacted Cl groups were capped by agitating the resin with 11 mL $CH_2Cl_2$-MeOH-DIEA (17:2:1) for 20 min. The resin was filtered and washed with $CH_2Cl_2$ (3×5 mL), MeOH (3×5 mL), and dried under vacuum for 1 h. The resin loading was determined by treating an aliquot (1-3 mg) of the dried resin with piperidine-DMF (1:4) and observing the UV absorbance of the piperidine-dibenzofulvene adduct at 301 nm ($\varepsilon$=7800 $M^{-1}$ $cm^{-1}$).

General procedure for manual SPPS. 5 mL fitted polypropylene syringes (Torviq) were used as reaction vessels for all manual SPPS and cleavage steps. Pre-loaded 2-CTC resin (0.05 mmol) was swelled in DMF for 30 min, drained, and treated with piperidine-DMF (1:4, 3 mL, 1×15 min). The resin was filtered and washed with DMF (2×3 mL) then $CH_2Cl_2$ (2×3 mL). In a separate flask, DIC (31 μL, 0.2 mmol) was added to a solution of Fmoc-AA-OH (0.2 mmol) and Oxyma Pure (0.2 mmol) in DMF (1.7 mL). Following a 5 min preactivation period, the resulting solution was added to the resin and the mixture agitated for 1 h. The resin was filtered and washed with DMF (3×2 mL) then $CH_2Cl_2$ (3×2 mL) and Kaiser ninhydrin8 test performed to determine reaction completion. Deprotection and coupling cycles were repeated until the desired peptide sequence was complete.

General procedure for automated SPPS. Linear peptides were synthesized on the 0.05 mmol scale using a PS3 peptide synthesizer (Gyros Protein Technologies). DIC, Oxyma Pure, and Fmoc-AA-OH (6 equiv, 0.3 mmol each) were used to accomplish couplings in 1 h, and Fmoc removal was achieved using piperidine-DMF (1:4, 2×5 min). Pre-loaded 2-chlorotrityl chloride resin (prepared as described above) was used for all syntheses.

General procedure for peptide cleavage. The peptide-linked resin was swelled in DMF (1×15 min), drained, and treated with 20% piperidine-DMF (1×15 min) to remove N-terminal Fmoc group. The resin was drained and washed with DMF (3×2 mL) then CH2Cl2 (3×2 mL) and a Kaiser ninhydrin8 test was performed to verify successful deprotection. The resin was treated with a 3 mL of a mixture of HFIP-$CH_2Cl_2$ (1:4) for 30 min and the filtrate concentrated under reduced pressure. The resulting residue was taken up in ~5 mL 50% $H_2O$—$CH_3CN$, frozen, and lyophilized to afford crude, side chain-protected, linear peptides that were used without further purification.

General procedure for peptide cyclization and global deprotection. To a solution of crude linear peptide (~0.05 mmol) and PyBop (78 mg, 0.15 mmol) in DMF (40 mL) was added DIEA (52 µL, 0.30 mmol). This solution was agitated overnight (17-24 h) and concentrated under reduced pressure. 10 mL of 50% H2O—CH3CN was added to the residue, the mixture vortexed, then centrifuged to afford a precipitate which was isolated by removal of the supernatant. The resulting solids were washed with an additional 10 mL 50% H2O—CH3CN, centrifuged, and isolated as before. The solids were frozen and lyophilized to remove residual solvent. Note: in rare cases where these conditions do not afford the cyclic peptides as precipitates, the crude peptides were purified at this stage by RP-HPLC ($CH_3CN$/$H_2O$ as the eluent). See Table S1 for more details. The crude material was treated with 3 mL of a mixture of TFA-$CH_2Cl_2$-TIPS (50:45:5) for 2 h, volatiles removed by a stream of air, and peptide precipitated with 2 mL of MTBE. Solids were collected, washed once with MTBE, dissolved in $H_2O$—$CH_3CN$, frozen, and lyophilized to afford cyclic peptides that were generally >90% pure.

HPLC Methods. HPLC analysis and purification was performed on an Agilent Technologies 1260 Infinity II preparative HPLC system using a 1260 variable wavelength detector (measuring at 214 nm and 254 nm). A Luna C18 reverse phase 5 µm, 150×4.6 mm column (Phenomenex) was used for purity analysis, and a Luna C18 reverse phase, 5 µm, 150×21.2 mm column (Phenomenex) was used for purification. Solvent A: water with 0.1% formic acid, solvent B: acetonitrile with 0.1% formic acid. For purity analysis, the following gradient was used: (A:B, 1 mL/min): 95:5, 0 min; 95:5, 1 min; 5:95, 20 min; 5:95, 25 min; 95:5, 30 min. For the preparatory HPLC runs, several different methods were employed. Method A2 (purification of linear peptide): (A:B, 20 mL/min): 95:5, 0 min; 95:5, 1 min; 5:95, 20 min; 5:95, 25 min; 95:5, 30 min. Method B2 (purification of cyclic peptide): (A:B, 20 mL/min): 95:5, 0 min; 95:5, 1 min; 5:95, 20 min; 5:95, 25 min; 95:5, 30 min. Method B3): (A:B, 20 mL/min): 95:5, 0 min; 95:5, 1 min; 60:40, 20 min; 5:95, 25 min; 95:5, 30 min. Further information about preparatory HPLC runs can be found in Table S1.

Mass Spectrometry. Mass spectra (MS) were recorded on an Advion Expression CMS single quadrupole mass spectrometer using electrospray ionization (ESI).

Antibacterial activity analysis. Antibacterial activity analysis for all bacteria was performed using the microdilution broth method as outlined by the Clinical and Laboratory Standards Institute (CLSI).9 Mueller Hinton Broth 2 (MH, Sigma-Aldrich, 90922) was used for all testing. Testing was performed as previously described.10 Turbidity (OD600) of the wells was determined using a SpectraMax iD3 platereader (Molecular Devices). For the compounds that hit during initial screens, minimum inhibitory concentrations were determined. A minimum of three biological replicates were performed. Ciprofloxacin was used as a control in these assays. Colistin was also used as a control in the colistin resistant strains.

Anticancer Testing. A549 non-small cell lung cancer cells (ATCC CCL-185) were obtained directly from ATCC and used within 30 passages. A549 cells were maintained in RPMI 1640 medium supplemented with 10% fetal bovine serum, 100 U/mL penicillin, and 100 ug/mL streptomycin. For anticancer testing, cells were seeded at 2000 cells per well in 96 well plates and allowed to adhere overnight. Cells were then treated with compound at 16 ug/mL (1% DMSO final) or vehicle control for 48 hours. Viability was assessed using Alamar Blue. Specifically, resazurin (Sigma Aldrich, R7017) was dissolved at 440 µM in sterile PBS. 20 µL was then added to each well and incubated for 4-8 h at 37° C. Fluorescence was measured using a SpectraMax iD3 platereader (Excitation: 550 nm, Emission 590 nm). Percent death was calculated by subtracting the background from all wells and setting 0% death to vehicle treated controls.

Hemolysis Assay. Hemolysis assays were based on a previously described method.11 Human Whole Blood was purchased from BioIVT and used prior to its expiration date. 100 µL of blood was aliquoted into a 1.5 mL Eppendorf tube and 500 µL of sterile 0.9% NaCl was added. Tubes were gently inverted to mix and then centrifuged at 500×g for 7 minutes. Supernatant was carefully removed and the pellet was washed 2× with 500 µL of 0.9% NaCl. The pellet was then resuspended in 800 µL of Red Blood Cell (RBC) buffer (10 mM Na2HPO4, 150 mM NaCl, 1 mM MgCl2, pH 7.4). To evaluate hemolytic activity of pNPs, 4 µL of a 1.6 mg/mL DMSO stock (54 µg/mL final working concentration) was transferred to a well of a 96 U-well plate. Negative control wells contained 4 µL of DMSO and positive controls contained 4 µL of 30% Triton X-100. To each well was then added 76 µL of RBC buffer and 40 µL of the resuspended red blood cells. This was incubated for 1 h at 37° C. The plate was then spun at 500×g for 5 min and the supernatants from each sample (75 µL) were transferred to a flat-well 96 well plate. The absorbance of these supernatants at 540 nm was then measured using a SpectraMax iD3 platereader. Percent hemolysis was calculated relative to the average absorbance values for the positive and negative controls. A minimum of three biological replicates was performed.

Bacterial Lysis Assay. Bacterial lysis assays were based on a previously described method.12 Briefly, 50 µL an overnight culture of *A. baumannii* was used to inoculate 5 mL of fresh MH medium. The culture was allowed to grow to mid-logarithmic phase (usually ~2 h). The bacteria were collected and washed 3 times with 5 mM HEPES (pH 7.4) supplemented with 20 mM glucose. After washing, bacteria were resuspended in 1 mL of 5 mM HEPES (pH 7.4) supplemented with 20 mM glucose and 100 mM KCl. *A. baumannii* suspensions of ~1E8 CFU were mixed with SYTOX Green (Invitrogen, 0.5 µM final concentration) and incubated for 15 minutes at room temperature in the dark. A 2× stock of compound or vehicle control was then mixed with the bacteria suspension and immediately transferred to a black clear bottom 96 well plate. Colistin was used as a positive control, and DMSO was used as a negative control. Bacterial cell lysis was monitored by the uptake of SYTOX green using a SpectraMax iD3 platereader (Excitation: 480 nm; Emission: 522 nm; read every 1 minute for 60 minutes).

Part of this disclosure has been published: Matthew A. Hostetler, et al., "Synthetic Natural Product Inspired Cyclic Peptides", *ACS Chem. Biol.* 2021, 16, 11, 2604-2611. https://doi.org/10.1021/acschembio.1c00641, the content of which is incorporated herein by reference in its entirety.

Additional disclosure can be found in Appendix-A, the content of which is incorporated herein by reference in its entirety.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

It is intended that that the scope of the present methods and compositions be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

CITED REFERENCES (1) Newman, D. J.; Cragg, G. M. Natural Products as Sources of New Drugs over the Nearly Four Decades from January 1981 to September 2019. *J. Nat. Prod.* 2020.

(2) Piel, J. Approaches to Capturing and Designing Biologically Active Small Molecules Produced by Uncultured Microbes. *Annu. Rev. Microbiol.* 2011, 65 (1), 431-453.

(3) Yu, X.; Sun, D. Macrocyclic Drugs and Synthetic Methodologies toward Macrocycles. *Molecules* 2013, 18 (6), 6230-6268.

(4) Jing, X.; Jin, K. A Gold Mine for Drug Discovery: Strategies to Develop Cyclic Peptides into Therapies. *Medicinal Research Reviews.* 2020.

(5) Gang, D.; Kim, D. W.; Park, H. S. Cyclic Peptides: Promising Scaffolds for Biopharmaceuticals. *Genes.* MDPI AG November 2018, p 557.

(6) Nielsen, D. S.; Shepherd, N. E.; Xu, W.; Lucke, A. J.; Stoermer, M. J.; Fairlie, D. P. Orally Absorbed Cyclic Peptides. *Chemical Reviews*. American Chemical Society June 2017, pp 8094-8128.

(7) Qian, Z.; Dougherty, P. G.; Pei, D. Targeting Intracellular Protein—Protein Interactions with Cell-Permeable Cyclic Peptides. *Current Opinion in Chemical Biology*. Elsevier Ltd June 2017, pp 80-86.

(8) White, C. J.; Yudin, A. K. Contemporary Strategies for Peptide Macrocyclization. *Nat. Chem.* 2011, 3 (7), 509-524.

(9) Villar, E. A.; Beglov, D.; Chennamadhavuni, S.; Porco, J. A.; Kozakov, D.; Vajda, S.; Whitty, A. How Proteins Bind Macrocycles. 2014.

(10) Rezai, T.; Yu, B.; Millhauser, G. L.; Jacobson, M. P.; Lokey, R. S. Testing the Conformational Hypothesis of Passive Membrane Permeability Using Synthetic Cyclic Peptide Diastereomers. *J. Am. Chem. Soc.* 2006, 128 (8), 2510-2511.

(11) Qian, Z.; Rhodes, C. A.; McCroskey, L. C.; Wen, J.; Appiah-Kubi, G.; Wang, D. J.; Guttridge, D. C.; Pei, D. *Angew. Chemie Int. Ed.* 2017, 56 (6), 1525-1529.

(12) Luo, Y.; Cobb, R. E.; Zhao, H. Recent Advances in Natural Product Discovery. *Current Opinion in Biotechnology*. Elsevier Ltd December 2014, pp 230-237.

(13) Henke, M. T.; Kelleher, N. L. Modern Mass Spectrometry for Synthetic Biology and Structure-Based Discovery of Natural Products. *Nat. Prod. Rep.* 2016, 33 (8), 942-950.

(14) Rutledge, P. J.; Challis, G. L. Discovery of Microbial Natural Products by Activation of Silent Biosynthetic Gene Clusters. *Nat. Rev. Microbiol.* 2015, 13 (8), 509-523.

(15) Wade, W. Unculturable Bacteria—The Uncharacterized Organisms That Cause Oral Infections. In *Journal of the Royal Society of Medicine*; Royal Society of Medicine Press, 2002; Vol. 95, pp 81-83.

(16) Blin, K.; Shaw, S.; Steinke, K.; Villebro, R.; Ziemert, N.; Lee, S. Y.; Medema, M. H.; Weber, T. AntiSMASH 5.0: Updates to the Secondary Metabolite Genome Mining Pipeline. *Nucleic Acids Res.* 2019, 47, 81-87.

(17) Skinnider, M. A.; Dejong, C. A.; Rees, P. N.; Johnston, C. W.; Li, H.; Webster, A. L. H.; Wyatt, M. A.; Magarvey, N. A. Genomes to Natural Products PRediction Informatics for Secondary Metabolomes (PRISM). *Nucleic Acids Res.* 2015, 43 (20), 9645-9662.

(18) Chu, J.; Vila-Farres, X.; Inoyama, D.; Ternei, M.; Cohen, L. J.; Gordon, E. A.; Reddy, B. V. B.; Charlop-Powers, Z.; Zebroski, H. A.; Gallardo-Macias, R.; et al. Discovery of MRSA Active Antibiotics Using Primary Sequence from the Human Microbiome. *Nat. Chem. Biol.* 2016, 12 (12), 1004-1006.

(19) Vila-Farces, X.; Chu, J.; Inoyama, D.; Ternei, M. A.; Lemetre, C.; Cohen, L. J.; Cho, W.; Reddy, B. V. B.; Zebroski, H. A.; Freundlich, J. S.; et al. *J. Am. Chem. Soc.* 2017, 139 (4), 1404-1407.

(20) Chu, J.; Vila-Farres, X.; Inoyama, D.; Gallardo-Macias, R.; Jaskowski, M.; Satish, S.; Freundlich, J. S.; Brady, S. F. Human Microbiome Inspired Antibiotics with Improved β-Lactam Synergy against MDR *ACS Infect. Dis.* 2018, 4 (1), 33-38.

(21) Vila-Farces, X.; Chu, J.; Ternei, M. A.; Lemetre, C.; Park, S.; Perlin, D. S.; Brady, S. F. An Optimized Synthetic-Bioinformatic Natural Product Antibiotic Sterilizes Multidrug-Resistant *Acinetobacter baumannii*-Infected Wounds. *mSphere* 2018, 3 (1).

(22) Chu, J.; Vila-Farres, X.; Brady, S. F. Bioactive Synthetic-Bioinformatic Natural Product Cyclic Peptides Inspired by Nonribosomal Peptide Synthetase Gene Clusters from the Human Microbiome. *J. Am. Chem. Soc.* 2019, 141 (40), 15737-15741.

(23) Chu, J.; Koirala, B.; Forelli, N.; Vila-Farces, X.; Ternei, M. A.; Ali, T.; Colosimo, D. A.; Brady, S. F. Synthetic-Bioinformatic Natural Product Antibiotics with Diverse Modes of Action. *J. Am. Chem. Soc.* 2020, 142 (33), 14158-14168.

(24) Pupin, M.; Esmaeel, Q.; Flissi, A.; Dufresne, Y.; Jacques, P.; Leclère, V. Norine: A Powerful Resource for Novel Nonribosomal Peptide Discovery. *Synthetic and Systems Biotechnology*. KeAi Communications Co. June 2016, pp 89-94.

(25) Grünewald, J.; Marahiel, M. A. Nonribosomal Peptide Synthesis. In *Handbook of Biologically Active Peptides*; Elsevier Inc., 2013; pp 138-149.

(26) Du, L.; Lou, L. PKS and NRPS Release Mechanisms. *Nat. Prod. Rep.* 2010, 27 (2), 255-278.

(27) Sieber, S. A.; Marahiel*, M. A. Molecular Mechanisms Underlying Nonribosomal Peptide Synthesis: Approaches to New Antibiotics. 2005.

(28) Süssmuth, R. D.; Mainz, A. Nonribosomal Peptide Synthesis-Principles and Prospects. *Angew. Chemie Int. Ed.* 2017, 56 (14), 3770-3821.

(29) Atanasov, A. G.; Zotchev, S. B.; Dirsch, V. M.; Supuran, C. T. *Nat. Rev. Drug Discov.* 2021 203 2021, 20 (3), 200-216.

(30) Thankachan, D.; Fazal, A.; Francis, D.; Song, L.; Webb, M. E.; Seipke, R. F. A Trans-Acting Cyclase Offloading Strategy for Nonribosomal Peptide Synthetases. *ACS Chem. Biol.* 2019, 14 (5), 845-849.

(31) Zhou, Y.; Lin, X.; Xu, C.; Shen, Y.; Wang, S.-P.; Liao, H.; Li, L.; Deng, H.; Lin, H.-W. Investigation of Penicillin Binding Protein (PBP)-like Peptide Cyclase and Hydrolase in Surugamide Non-Ribosomal Peptide Biosynthesis. *Cell Chem. Biol.* 2019, 26 (5), 737-744.e4.

(32) Kuranaga, T.; Matsuda, K.; Sano, A.; Kobayashi, M.; Ninomiya, A.; Takada, K.; Matsunaga, S.; Wakimoto, T. Total Synthesis of the Nonribosomal Peptide Surugamide B and Identification of a New Offloading Cyclase Family. *Angew. Chemie Int. Ed.* 2018, 57 (30), 9447-9451.

(33) Matsuda, K.; Zhai, R.; Mori, T.; Kobayashi, M.; Sano, A.; Abe, I.; Wakimoto, T. Heterochiral Coupling in Non-Ribosomal Peptide Macrolactamization. *Nat. Catal.* 2020, 3, 507-515.

(34) Hwang, S.; Le, L. T. H. L.; Jo, S.-I.; Shin, J.; Lee, M. J.; Oh, D.-C. Pentaminomycins C-E: Cyclic Pentapeptides as Autophagy Inducers from a Mealworm Beetle Gut Bacterium. *Microorganisms* 2020, 8 (9), 1390.

(35) Mudalungu, C. M.; Von Törne, W. J.; Voigt, K.; Rückert, C.; Schmitz, S.; Sekurova, O. N.; Zotchev, S. B.; Süssmuth, R. D. Noursamycins, Chlorinated Cyclohexapeptides Identified from Molecular Networking of *Streptomyces noursei* NTR-SR4. *J. Nat. Prod.* 2019, 82 (6), 1478-1486.

(36) Kaweewan, I.; Komaki, H.; Hemmi, H.; Kodani, S. Isolation and Structure Determination of New Antibacterial Peptide Curacomycin Based on Genome Mining. *Asian J. Org. Chem.* 2017, 6 (12), 1838-1844.

(37) Altschul, S. F.; Gish, W.; Miller, W.; Myers, E. W.; Lipman, D. J. Basic Local Alignment Search Tool. *J. Mol. Biol.* 1990, 215 (3), 403-410.

(38) Tietz, J. I.; Schwalen, C. J.; Patel, P. S.; Maxson, T.; Blair, P. M.; Tai, H.-C.; Zakai, U. I.; Mitchell, D. A. A New Genome-Mining Tool Redefines the Lasso Peptide Biosynthetic Landscape. *Nat. Chem. Biol.* 2017, 13 (5), 470-478.

(39) Skinnider, M. A.; Johnston, C. W.; Gunabalasingam, M.; Merwin, N. J.; Kieliszek, A. M.; MacLellan, R. J.; Li, H.; Ranieri, M. R. M.; Webster, A. L. H.; Cao, M. P. T.; et al. *Nat. Commun.* 2020, 11 (1), 1-9.

(40) Caboche, S.; Leclère, V.; Pupin, M.; Kucherov, G.; Jacques, P. Diversity of Monomers in Nonribosomal Peptides: Towards the Prediction of Origin and Biological Activity. *J. Bacteriol.* 2010, 192 (19), 5143-5150.

(41) Huigens, R. W.; Morrison, K. C.; Hicklin, R. W.; Flood, T. A.; Richter, M. F.; Hergenrother, P. J. *Nat. Chem.* 2013, 5 (3), 195-202.

(42) Backman, T. W. H.; Cao, Y.; Girke, T. ChemMine Tools: An Online Service for Analyzing and Clustering Small Molecules. *Nucleic Acids Res.* 2011, 39 (suppl), W486-W491.

(43) Gerlt, J. A. Genomic Enzymology: Web Tools for Leveraging Protein Family Sequence-Function Space and Genome Context to Discover Novel Functions. *Biochemistry* 2017, 56 (33), 4293-4308.

(44) Navarro-Muñoz, J. C.; Selem-Mojica, N.; Mullowney, M. W.; Kautsar, S. A.; Tryon, J. H.; Parkinson, E. I.; De Los Santos, E. L. C.; Yeong, M.; Cruz-Morales, P.; Abubucker, S.; et al. A Computational Framework to Explore Large-Scale Biosynthetic Diversity. *Nat. Chem. Biol.* 2020, 16 (1), 60-68.

(45) Merrifield, R. B. Solid Phase Peptide Synthesis. I. The Synthesis of a Tetrapeptide. *J. Am. Chem. Soc.* 1963, 85 (14), 2149-2154.

(46) Subirós-Funosas, R.; Prohens, R.; Barbas, R.; El-Faham, A.; Albericio, F. Oxyma: An Efficient Additive for Peptide Synthesis to Replace the Benzotriazole-Based HOBt and HOAt with a Lower Risk of Explosion. *Chemistry (Easton)*. 2009, 15 (37), 9394-9403.

(47) Patel, J. B.; Cockerill, F. R.; Bradford, P. A.; Elipoulos, G. M.; Hindler, J. A.; Jenkins, S. G.; Lewis, J. S.; Limbago, B.; Miller, L. A.; Nicolau, D. P.; et al. *Methods for Dilution Antimicrobial Susceptibilities Tests for Bacteria That Grow Aerobically; Tenth Edition*, CLSI docum.; Clinical and Laboratory Standards Institute: Wayne, PA, 2015.

(48) Tommasi, R.; Brown, D. G.; Walkup, G. K.; Manchester, J. I.; Miller, A. A. ESKAPEing the Labyrinth of Antibacterial Discovery. *Nature Reviews Drug Discovery*. Nature Publishing Group Aug. 1, 2015, pp 529-542.

(49) Payne, D. J.; Gwynn, M. N.; Holmes, D. J.; Pompliano, D. L. *Nat. Rev. Drug Discov.* 2007, 6 (1), 29-40.

(50) Yang, H.; Chen, K. H.; Nowick, J. S. Elucidation of the Teixobactin Pharmacophore. *ACS Chem. Biol.* 2016, 11 (7), 1823-1826.

(51) Jad, Y. E.; Acosta, G. A.; Naicker, T.; Ramtahal, M.; El-Faham, A.; Govender, T.; Kruger, H. G.; Torre, B. G. de la; Albericio, F. Synthesis and Biological Evaluation of a Teixobactin Analogue. *Org. Lett.* 2015, 17 (24), 6182-6185.

(52) Parmar, A.; Iyer, A.; Prior, S. H.; Lloyd, D. G.; Goh, E. T. L.; Vincent, C. S.; Palmai-Pallag, T.; Bachrati, C. Z.; Breukink, E.; Madder, A.; et al. *Chem. Sci.* 2017, 8 (12), 8183.

(53) Li, Y.-X.; Zhong, Z.; Zhang, W.-P.; Qian, P.-Y. Discovery of Cationic Nonribosomal Peptides as Gram-Negative Antibiotics through Global Genome Mining. *Nat. Commun.* 2018 91 2018, 9 (1), 1-9.

(54) Gallardo-Godoy, A.; Muldoon, C.; Becker, B.; Elliott, A. G.; Lash, L. H.; Huang, J. X.; Butler, M. S.; Pelingon, R.; Kavanagh, A. M.; Ramu, S.; et al. Activity and Predicted Nephrotoxicity of Synthetic Antibiotics Based on Polymyxin B. *J. Med. Chem.* 2016, 59 (3), 1068-1077.

(55) Rajasekaran, G.; Kim, E. Y.; Shin, S. Y. LL-37-Derived Membrane-Active FK-13 Analogs Possessing Cell Selectivity, Anti-Biofilm Activity and Synergy with Chloramphenicol and Anti-Inflammatory Activity. *Biochim. Biophys. Acta—Biomembr.* 2017, 1859 (5), 722-733.

What is claimed is:

1. A method for treating a patient in need thereof, comprising administering a pharmaceutical composition comprising a bioactive molecule selected from the group consisting of:

pNP-80

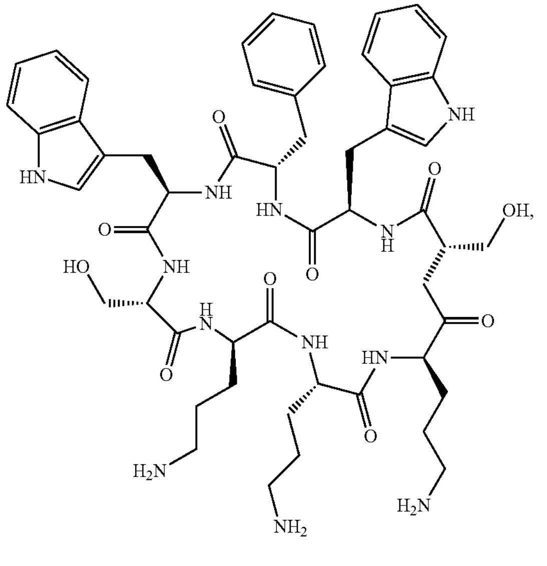

-continued
pNP-51
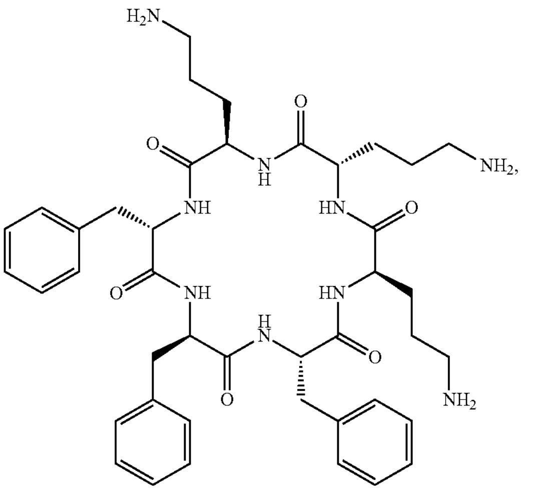
pNP-111
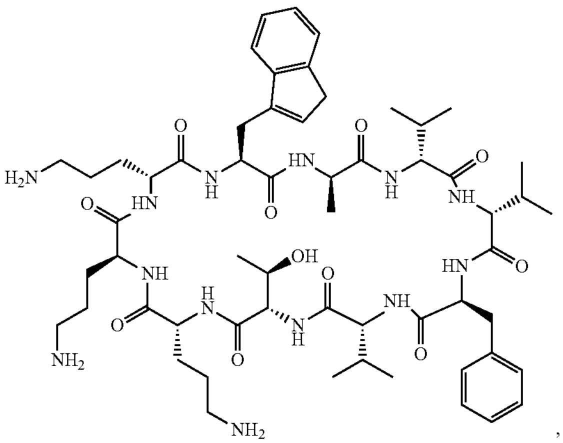
,
pNP-66
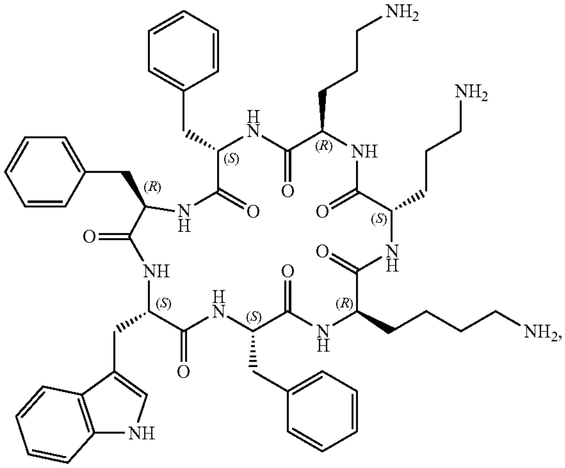
CS-1-07
-continued
pNP-23
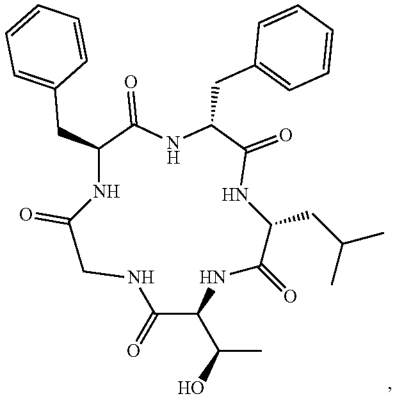
,
pNP-43
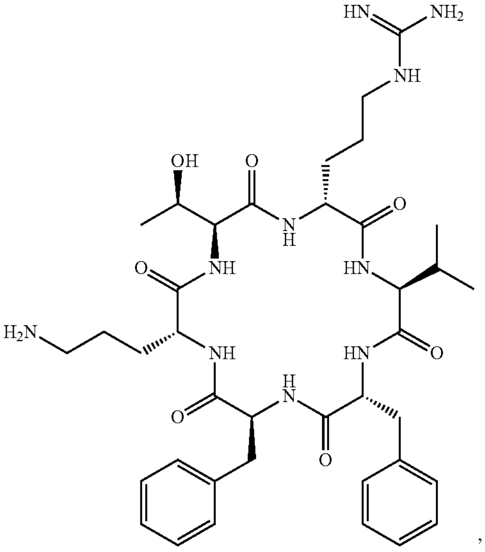
, and
pNP-40
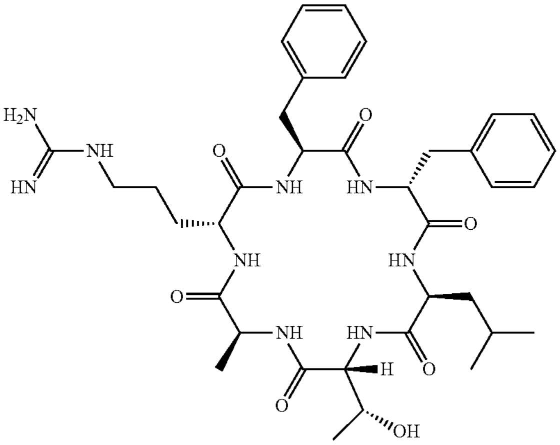
or a pharmaceutically acceptable salt thereof, with a carrier, diluent or excipient, to a patient in need of therapeutic treatment, wherein said bioactive molecules are antibiotics.
* * * * *